United States Patent [19]

Baxter

[11] 4,323,569
[45] Apr. 6, 1982

[54] β-LACTAM ANTI-BACTERIAL, COMPOSITIONS CONTAINING THEM AND A PROCESS FOR THEIR PREPARATION

[75] Inventor: Andrew J. G. Baxter, Hull, England
[73] Assignee: Beecham Group Limited, England
[21] Appl. No.: 68,893
[22] Filed: Aug. 23, 1979

[30] Foreign Application Priority Data

Aug. 25, 1978 [GB] United Kingdom ............... 34643/78

[51] Int. Cl.³ .................. C07D 487/04; A61K 31/505
[52] U.S. Cl. ............................ 424/251; 260/245.2 T; 260/239 A; 544/316; 544/319
[58] Field of Search ............... 544/333, 316, 326, 319; 260/245.2 T; 424/251

[56] References Cited
FOREIGN PATENT DOCUMENTS 1627 5/1979 European Pat. Off. ....... 60/245.2 T
1628 5/1979 European Pat. Off. ....... 260/245 T Primary Examiner—Mary C. Lee
Attorney, Agent, or Firm—Jacobs & Jacobs

[57] ABSTRACT

The compounds of the formula (II):

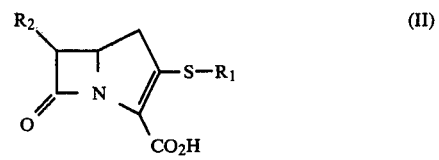

and salts and esters thereof wherein $R_1$ is a pyrimidyl group, or a pyrimidyl group substituted by one or two lower alkyl groups, or by a lower alkoxy group or by a lower acyloxy group; and $R_2$ is a hydrogen atom or a group $CR_3R_4R_5$ wherein $R_3$ is a hydrogen atom or a hydroxy group; $R_4$ is a hydrogen atom or a lower alkyl group; and $R_5$ is a hydrogen atom or a lower alkyl group, a benzyl group, a phenyl group or is joined to $R_4$ to form part of a $C_{5-7}$ carbocyclic ring, have been found to be anti-bacterial-agents. Their preparation and use is described.

86 Claims, No Drawings

β-LACTAM ANTI-BACTERIAL, COMPOSITIONS CONTAINING THEM AND A PROCESS FOR THEIR PREPARATION

The present invention relates to β-lactam antibacterials, to compositions containing them, to the process for their preparation and to compounds useful as intermediates in that process.

Belgian Pat. No. 860962 discloses a vast group of compounds of the general formula (I):

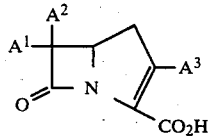

and their salts and esters wherein $A^1$, $A^2$ and $A^3$ may be hydrogen or various optionally substituted hydrocarbon groups. The activity of these compounds was not illustrated. A further and considerably different group of carbapenems has now been discovered which carry a thioether moiety on the 5-membered ring. These compounds have proved to possess gram-negative and gram-positive antibacterial activity so that they are of interest as broad spectrum antibacterial agents.

The present invention provides the compounds of the formula (II):

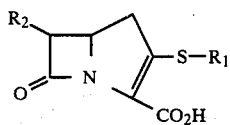

and salts and esters thereof wherein $R_1$ is pyrimidyl group, or a pyrimidyl group substituted by one or two lower alkyl groups, or by a lower alkoxy group or by a lower acyloxy group; and $R_2$ is a hydrogen atom or a group $CR_3R_4R_5$ wherein $R_3$ is a hydrogen atom or a hydroxy group; $R_4$ is a hydrogen atom or a lower alkyl group; and $R_5$ is a hydrogen atom or a lower alkyl group, a benzyl group, a phenyl group or is joined to $R_4$ to form part of a $C_{5-7}$ carbocyclic ring.

Aptly $R_1$ is a pyrimidyl group, or a pyrimidyl group substituted by a lower alkyl group; and $R_2$ is a hydrogen atom or a group $CR_3R_4R_5$ wherein $R_3$ is a hydrogen atom or a hydroxy group; $R_4$ is a hydrogen atom or a lower alkyl group; and $R_5$ is a hydrogen atom or a lower alkyl group, a benzyl group, a phenyl group or is joined to $R_4$ to form part of a $C_{5-7}$ carbocyclic ring.

Suitably $R_1$ is a pyrimidyl, methylpyrimidyl, dimethylpyrimidyl, ethylpyrimidyl, diethylpyrimidyl, acetoxypyrimidyl or the like group.

More suitably $R_1$ is a 2-pyrimidyl. Also more suitably $R_1$ is a dimethyl-4-pyrimidyl or methyl-2-pyrimidyl group.

Preferred values of $R_1$ are the 2-pyrimidyl, 4-pyrimidyl, 4-6-dimethyl-2-pyrimidyl and the 4-methyl-2-pyrimidyl groups.

We have found that compounds with these values of $R_1$ are readily synthesised and have particularly good antibacterial properties.

One suitable sub-group of compounds of the formula (II) is that of the formula (III):

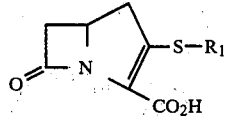

and salts and esters thereof wherein $R_1$ is as defined in relation to formula (II). This sub-group is particularly preferred.

A further suitable sub-group of compounds of the formula (II) is that of formula (IV):

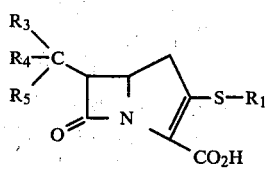

and salts and esters thereof wherein $R_3$, $R_4$ and $R_5$ are as defined in relation to formula (II).

Suitably $R_3$ is a hydrogen atom. Suitably $R_3$ is a hydroxy group. Suitably values for $R_5$ include the hydrogen atom and the methyl, ethyl, n-propyl or phenyl group.

Suitable values for $R_4$ include the hydrogen atom and the methyl, ethyl and n-propyl groups. Favourably $R_4$ is a hydrogen atom or a methyl group. Favourably $R_5$ is a hydrogen atom or a methyl group.

A suitable sub-group of compounds of the formula (IV) is that of the formula (V):

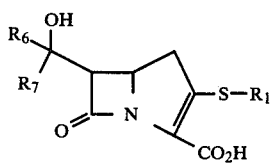

and salts and esters thereof wherein $R_1$ is as defined in relation to formula (II), $R_6$ is a hydrogen atom or a lower alkyl group and $R_7$ is a hydrogen atom or a lower alkyl group.

Suitably $R_6$ is a hydrogen atom or a methyl or ethyl group. Suitably $R_7$ is a hydrogen atom or a methyl or ethyl group.

Favourably the $C(OH)(R_6)R_7$ moiety is a $C(CH_3)_2OH$, $CH(CH_3)OH$ or $CH(C_2H_5)OH$ group. The $CH(CH_3)OH$ group is particularly preferred for $C(OH)(R_6)R_7$.

It is to be realised that compounds of the formula (V) wherein $R_6$ and $R_7$ have different values may exist in either the 8R or the 8S form. If desired these compounds may be presented as mixtures of the 8R and 8S forms although it is not normally preferred to so do.

It will be realised from the foregoing that a preferred group of compounds of the formula (V) is that wherein the $C(OH)(R_6)R_7$ moiety is a $CH(CH_3)OH$ group and $R_1$ is a 2-pyrimidyl, 4-pyrimidyl, 4,6-dimethyl-2-pyrimidyl or 4-methyl-2-pyrimidyl group.

A preferred compound is 5(R,S), 6(S,R) 3-(4,6-dimethyl-2-pyrimidylthio)-6-(IR-hydroxyethyl)-7-oxo-1-azabicyclo[3,2,0]hept-2-ene-2-carboxylate.

A further preferred compound is 5(R,S), 6(S,R) 3-(2-pyrimidylthio)-6-(1R-hydroxyethyl)-7-oxo-1-azabicyclo[3,2,0]hept-2-ene-2-carboxylate.

Other apt compounds include:
benzyl 3-(2-pyrimidylthio)-7-oxo-1-azabicycl[3,2,0-]hept-2-ene-2-carboxylate,p-nitrobenzyl 3-(2-pyrimidylthio)-7-oxo-1-azabicyclo[3,2,0]hept-2-ene-2-carboxylate, phthalidyl 3-(4,6-dimethyl-2-pyrimidylthio)-7-oxo-1-azabicyclo[3,2,0]hept-2-ene-2-carboxylate, phthalidyl 3-(2-pyrimidylthio)-7-oxo-1-azabicyclo[3,2,0]hept-2-ene-2-carboxylate, benzyl 3-(4,6-dimethyl-2-pyrimidylthio)-7-oxo-1-azabicyclo[3,2,0]hept-2-ene-2-carboxylate, p-nitrobenzyl 3-(4,6-dimethyl-2-pyrimidylthio)-7-oxo-1-azabicyclo [3,2,0]hept-2-ene-2-carboxylate, benzyl 3-(4-pyrimidylthio)-7-oxo-1-azabicyclo[3,2,0]hept-2-ene-2-carboxylate, p-nitrobenzyl 3-(4-pyrimidylthio)-7-oxo-1-azabicyclo[3,2,0]hept-2-ene-2-carboxylate, 3-(2-pyrimidylthio)-7-oxo-1-azabicyclo[3,2,0]hept-2-ene-2-carboxylate, 3-(4,6-dimethyl-2-pyrimidylthio)-7-oxo-1-azabicyclo[3,2,0]hept-2-ene-2-carboxylate, p-nitrobenzyl 3-(4-methyl-2-pyrimidylthio)-7-oxo-1-azabicyclo[3,2,0]-hept-2-ene-2-carboxylate, 3-(4-methyl-2-pyrimidylthio)-7-oxo-1-azabicyclo[3,2,0-]hept-2-ene-2-carboxylate, 5(R,S), 6(S,R)3-(4-pyrimidylthio)-6-(1R-hydroxyethyl)-7-oxo-1-azabicyclo[3,2,0]hept-2-ene-2-carboxylate, and 5(R,S), 6(S,R) 3-(4-methyl-2-pyrimidylthio)-(1R-hydroxyethyl)-7-oxo-1-azabicyclo[3,2,0]hept-2-ene-2-carboxylate.

Compounds of this invention have the surprising advantage of improved stability and this is reflected in their improved in-vivo stability over analogous compounds containing a pyridyl group.

Yet another apt sub-group of compounds of the formula (III) is that of the formula (VI):

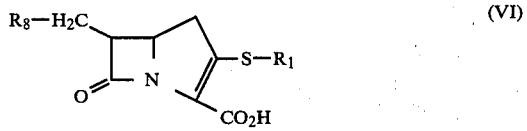

and salts and esters thereof wherein $R_1$ is as defined in relation to formula (II) and $R_8$ is a hydrogen atom or a methyl or ethyl group.

The compounds of the formulae (II)–(VI) tend to be more active than corresponding esters and are thus particularly suitable.

Compounds of the formulae (II)–(VI) which are esterified have activity in their own right but less than the corresponding acids so in general it is preferred that esters of this invention are those which are convertible to a corresponding salt by chemical or biological means.

Suitably the acid is esterified by a group of the sub-formulae (a), (b), (c) or (d):

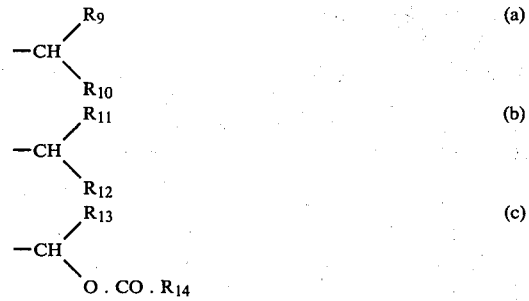

wherein $R_9$ is a hydrogen atom or an alkyl, alkenyl or alkynyl group of up to 3 carbon atoms; $R_{10}$ is a hydrogen atom or a methyl group; $R_{11}$ is a phenyl group or a phenyl group substituted by a fluorine, chlorine or bromine atom or a nitro, methyl or methoxy group; $R_{12}$ is a hydrogen atom or a phenyl group or a phenyl group substituted by a fluorine, chlorine or bromine atom or a nitro, methyl or methoxy group; $R_{13}$ is a hydrogen atom or a methyl group and $R_{14}$ is a lower alkyl, phenyl or lower alkoxy group or $R_{13}$ is joined to $R_{14}$ to form a phthalidyl group; and $R_{15}$ is a lower alkyl, phenyl, chlorophenyl or nitrophenyl group.

Favourably $R_9$ is a hydrogen atom or a methyl, ethyl, vinyl or acetanyl group. Favourably $R_{10}$ is a hydrogen atom. Favourably $R_{11}$ is a phenyl, p-bromophenyl, p-methoxyphenyl or p-nitrophenyl group. Favourably $R_{12}$ is a hydrogen atom. Favourably $R_{14}$ is a methyl, t-butyl or ethoxy group or is joined to $R_{13}$. Favourably $R_{15}$ is a methyl group.

Particularly apt groups of the sub-formula (a) include the methyl and ethyl groups.

Particularly apt groups of the sub-formula (b) include the benzyl and p-nitrobenzyl groups.

Particularly apt groups of the sub-formula (c) include the acetoxymethyl, pivaloyloxymethyl, α-ethoxycarbonyloxyethyl and phthalidyl groups.

A particularly apt group of the sub-formula (d) is the methoxymethyl group.

A preferred esterifying group is p-nitrobenzyl.

A further preferred esterifying group is the phthalidyl group.

A preferred embodiment of this invention is when the compounds of the formula (II) are in zwitterionic form.

The compounds of the formula (IV)–(VI) may have the cis-configuration about the β-lactam ring. The compounds of the formulae (IV)–(VI) may alternatively have the trans-configuration about the β-lactam ring. If desired these compounds may be presented as mixtures of cis- and trans- compounds although it is not normally preferred to so do.

The compounds of the formula (II)–(VI) are more conveniently provided as mixtures of 5R and 5S forms.

It is believed that the more active isomer from these mixtures is that which exemplified in relation to formula (II) has the configuration shown in formula (IIx):

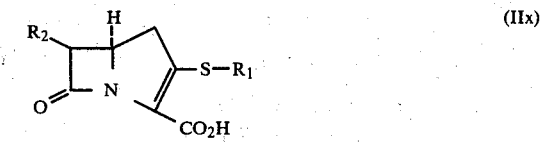

This invention also provides an antibacterial pharmaceutical composition which comprises a compound of the formula (II)–(VI) or a salt or ester thereof and a pharmaceutically acceptable carrier.

Most suitably the composition will comprise the compound of the formula (II)–(VI) per se.

Most suitably the composition will be in unit dosage form and will comprise 25–1000 mg and more usually 50–500 mg of a compound of the formula (II)–(VI).

The compositions of this invention may beneficially also comprise a penicillin or cephalosporin. Certain particularly suitable penicillins for use in these compositions include amoxycillin trihydrate and sodium amoxycillin.

The compositions of this invention may be used for the treatment of bacterial infections due to susceptible bacteria such as gram positive bacteria such as *Staphylococcus aureus* or gram negative bacteria such as *Escherichia coli* or *Klebsiella aerogenes*.

The present invention also provides a method for the treatment of bacterial infections in humans or domestic mammals which comprises the administration of a composition of this invention.

The compositions may be administered in conventional manner, for example orally or parenterally or in cattle by intramammary administration (for the treatment of mastitis).

The compositions may be formulated as described in Belgian Patent Specification No. 860962 or U.S. Ser. Nos. 887,841 or 887,844 the disclosures of which with respect to compositions are included herein by reference.

The compounds of the present invention may be prepared by reaction sequences such as those outlined in Schemes 1, 2, 3 and 4. In the schemes PNB means paranitrobenzyl. Although Schemes 1 and 2 show the preparation of compounds with a 6-CH(CH$_3$)OH group via compounds with a 6-CH(CH$_3$)OCO$_2$PNB group it should be appreciated that other moieties R$_3$ may be included at the 6-position.

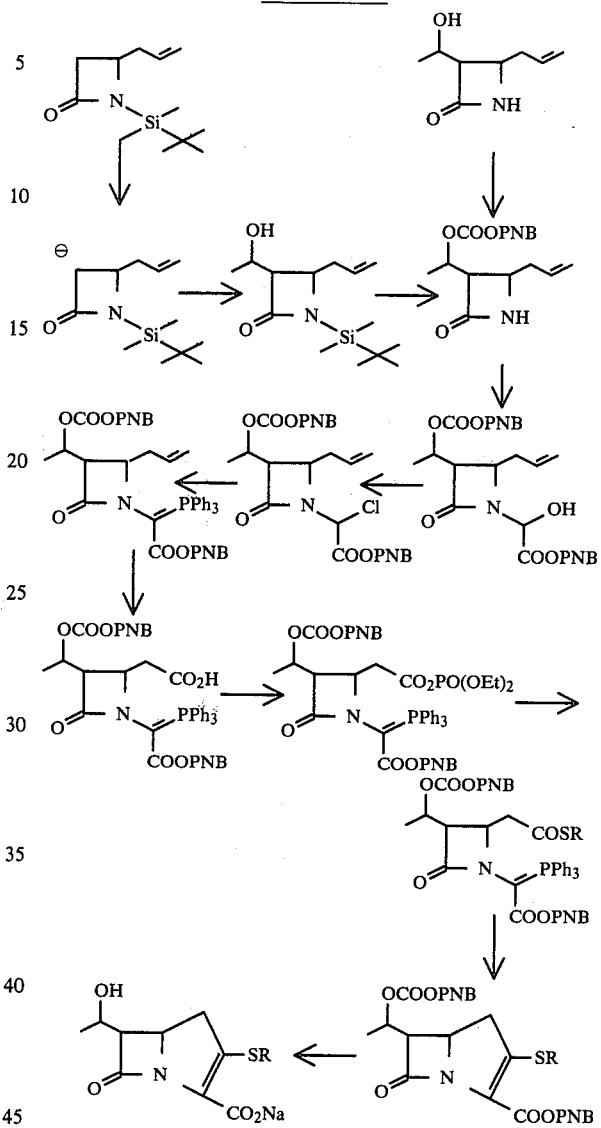

SCHEME 1

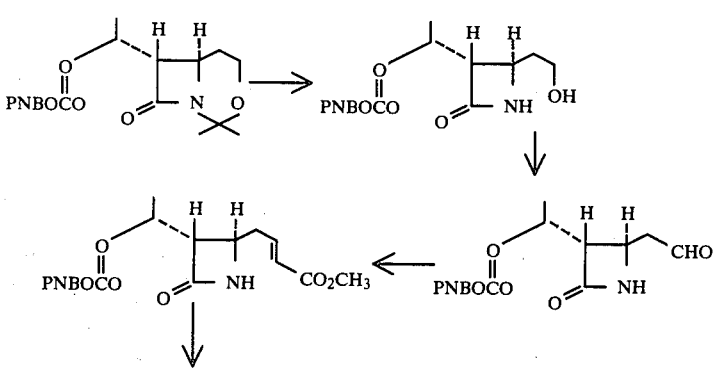

Scheme 2

Scheme 2
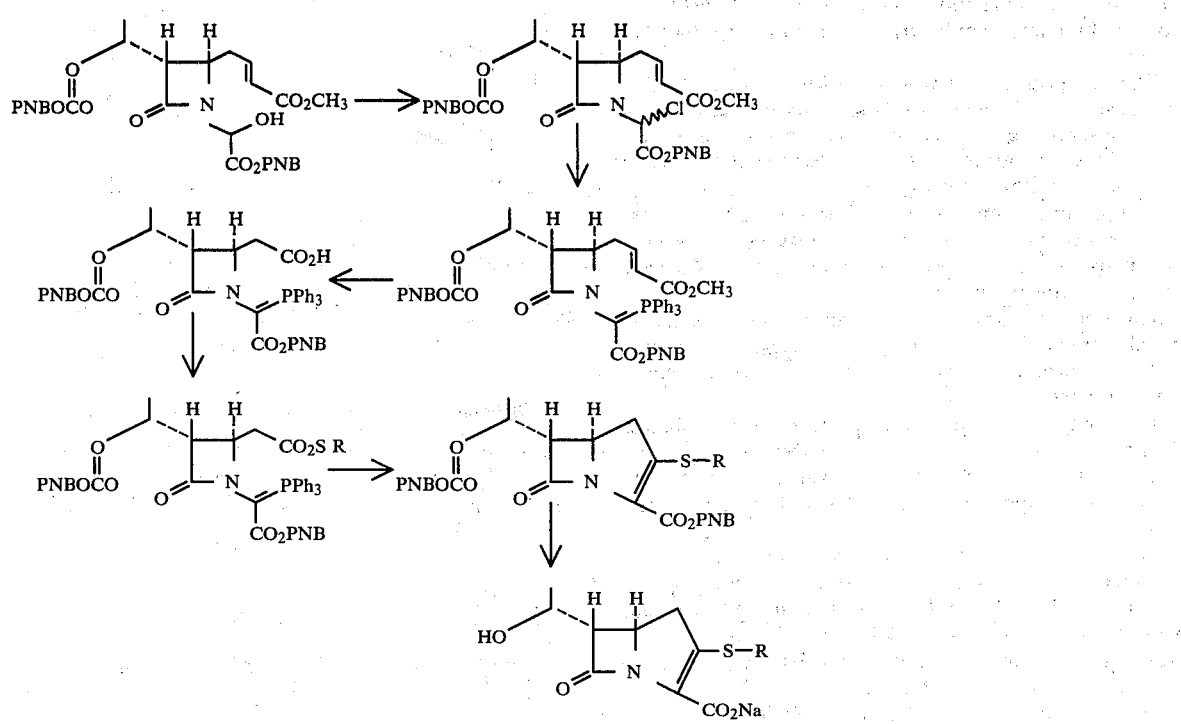
Scheme 3
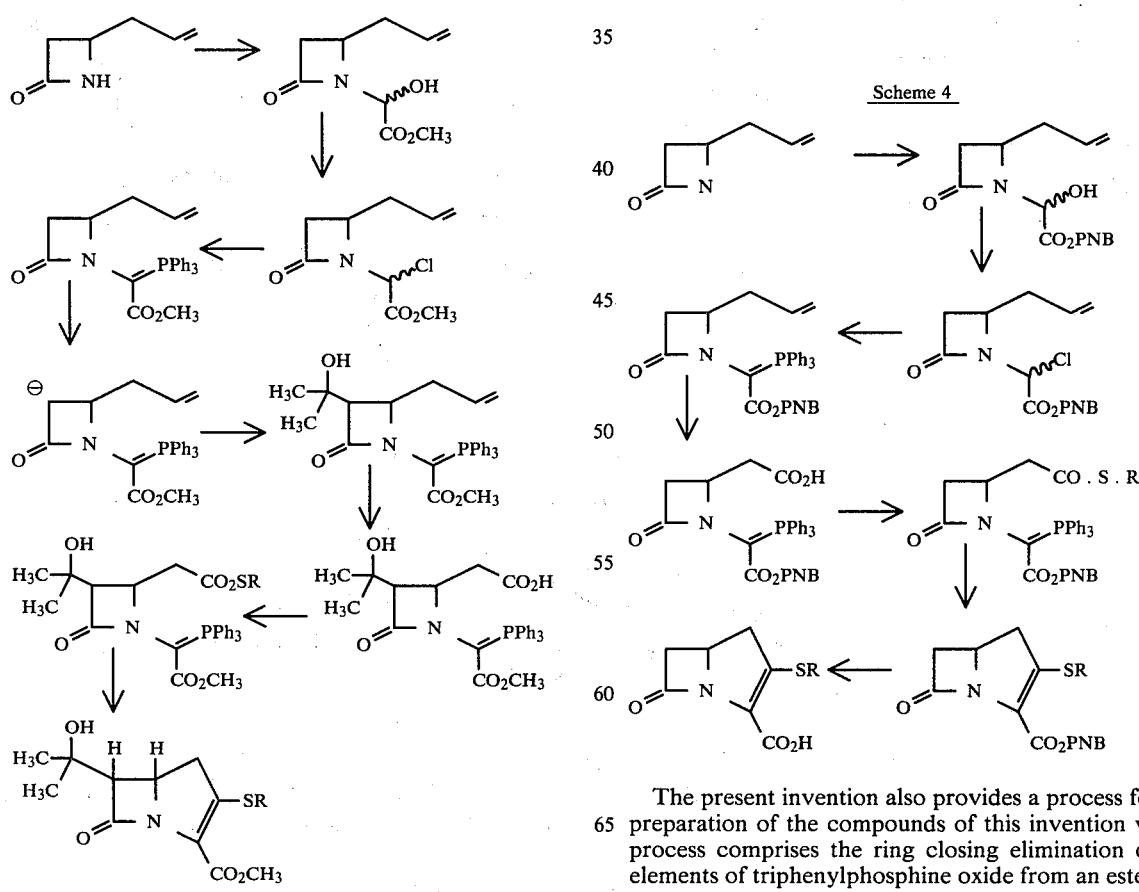
Scheme 4
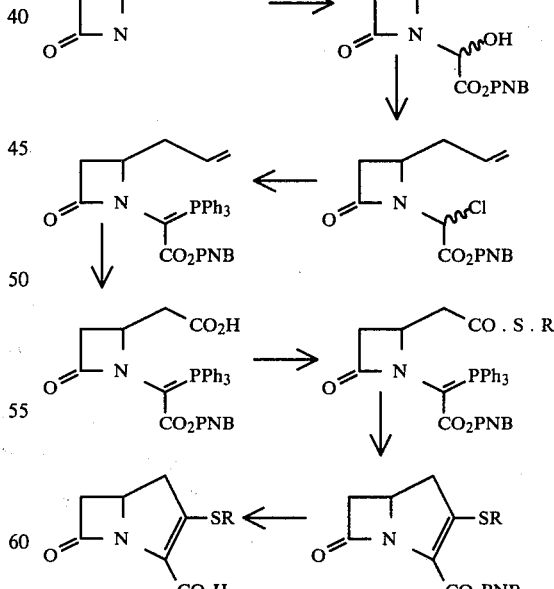
The present invention also provides a process for the preparation of the compounds of this invention which process comprises the ring closing elimination of the elements of triphenylphosphine oxide from an ester of a compound of the formula (VII):

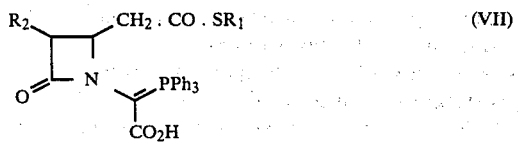

(VII)

wherein $R_1$ and $R_2$ are as defined in relation to formula (II) and thereafter if desired (a) isolating the ester thus produced, (b) where desired de-esterifying a cleavable ester to form a free acid or its salt, (c) optionally converting the salt so formed into a free acid or optionally converting the acid so formed into a salt, and (d) optionally converting a salt into an alternative ester.

If desired a hydroxy group optionally present in $R_2$ may be protected during the reactions described herein for example as a p-nitrobenzyloxycarbonyl derivative. This may be removed later by hydrogenation.

The ring closure is normally brought about by heating the ester of the compound of the formula (VII) in an inert solvent; for example temperatures of 90°–120° C. and more suitably 100°–110° C. may be employed in a solvent such as toluene or the like. The reaction is best carried out under dry conditions under an inert gas.

The ester of the compound (II) produced may be isolated by any standard method such as fractional crystallisation, counter current separation or chromatography. We have found that it is most convenient to separate the desired product by column chromatography.

Any convenient ester may be used in the process of this invention. Since it is frequently desirable to form a salt of compounds (II), the ester employed is preferably one which is readily converted to the parent acid or its salt by mild methods of hydrogenolysis. In a further aspect therefore the invention includes a process for preparing a salt or free acid of a compound (II) which process comprises de-esterifying an ester of a compound of formula (II). Particularly suitable esters for use in this process include benzyl esters, optionally substituted in the para position by a lower alkoxy or nitro group or a halogen atom.

A preferred ester for use in this process is the p-nitrobenzyl ester.

Esters of compounds (II) may be de-esterified by conventional methods of hydrogenolysis.

Suitable methods include hydrogenation in the presence of a transition metal catalyst. The pressure of hydrogen used in the reaction may be low, medium or high but in general an approximately atmospheric or slightly super-atmospheric pressure of hydrogen is preferred. The transition metal catalyst employed is preferably palladium on charcoal or on calcium carbonate. The hydrogenation may be effected in any inert solvent in which the ester is soluble such as aqueous dioxan or the like. If this hydrogenation is carried out in the presence of a base then a salt of compounds (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4OCOCH_3$, pH7 phosphate buffer. If no base is present, which is preferred, then hydrogenation leads to the preparation of an acid within formula (II). The acid may later be neutralised if desired to yield a salt. Suitable bases which may be used to neutralise acids within formula (II) include LiOH, NaOH, $NaHCO_3$, KOH, $Ca(OH)_2$ and $Ba(OH)_2$.

The salts of acids (II) may be converted to esters in conventional manner, for example by reaction with a reactive halide such as bromophthalide in solution in dimethylformamide or like solvent.

The ester of the compound of the formula (VII) may be prepared by the reaction of a corresponding ester of a compound of the formula (VIII):

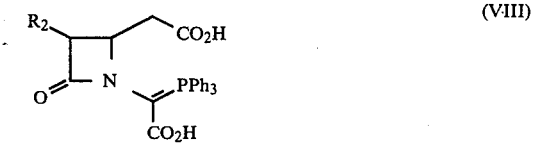

(VIII)

wherein $R_2$ is as defined in relation to formula (II) with a diloweralkylphosphorochloridate or thionylchloride and a triloweralkylamine followed by reaction with a thallium I, lithium, silver or sodium salt of the compound of the formula (IX):

$$L^{+-}SR_1 \qquad (IX)$$

in the presence of an organic base.

Preferably the compound of the formula (IX) is used in the form of its thallium (I), lithium or sodium salt.

Organic bases for use together with the compound of the formula (IX) are preferably tertiary amines such as triloweralkylamines or aromatic bases such as pyridine.

A particularly suitable diloweralkylphosphorochloridate is diethylphosphorochloridate.

A particularly suitable triloweralkylamine is triethylamine. Pyridine is also particularly suitable.

The reaction is generally carried out in an inert organic solvent such as tetrahydrofuran or acetonitrile at a non-extreme temperature such as 0° to 40° C. for example 15°–25° C.

The ester of the compound of the formula (VIII) may be prepared by the reaction of an ester of the compound of the formula (X):

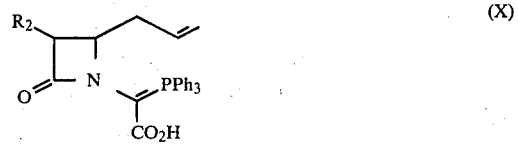

(X)

wherein $R_2$ is as defined as in relation to formula (II) with ozone in the presence of trifluoroacetic acid followed by m-chloroperbenzoic acid.

The ozonolysis is generally performed at a depressed temperature such as −40° to −80° C., for example about −70° C. and in solution in an inert solvent such as methylene chloride. Excess ozone is removed by flushing with an inert gas and thereafter a solution of the peracid is added to the reaction mixture.

The ester of the compound of the formula (X) may be prepared from the corresponding ester of a compound of the formula (XI):

(XI)

wherein $R_2$ is as defined in relation to formula (II) with triphenylphosphine.

This reaction is normally effected in the presence of at least one equivalent of a base of relatively low nucleophilicity such as 2,6-lutidine at an ambient temperature in a dry solvent such as dioxan, tetrahydrofuran or the like.

The ester of the compound of the formula (XI) may be prepared from the corresponding ester of the carbinol of the formula (XII):

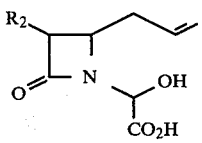
(XII)

wherein $R_2$ is as defined in relation to formula (II) by reaction with thionyl chloride.

This reaction is also normally effected in the presence of at least one equivalent of a base of relatively low nucleophilicity in a dry solvent such as dioxan or tetrahydrofuran but in this instance the reaction is performed at a depressed temperature, for example $-30°$ to $-10°$ C.

The preceding carbinol may be prepared by the reaction of a compound of the formula (XIII):

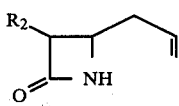
(XIII)

wherein $R_2$ is as defined in relation to formula (II) with a glyoxylic acid ester.

Normally this reaction is carried out in an inert solvent at an elevated temperature, for example in dry benzene under reflux.

The esters of the compounds of the formula (XII) may also be prepared by esterification of a salt of the compound of the formula (XII) in conventional manner. Suitable methods include the reaction of alkali metal salt such as a sodium or potassium salt with a reactive halide or sulphonate ester such as a bromide, chloride, mesylate, tosylate or the like. Such esterifications may be carried out under conventional conditions, for example in dimethylformamide at room temperature.

The salt of compound of the formula (XII) may be prepared by neutralisation of the acid of the formula (XII), for example with an alkali metal carbonate or bicarbonate, for example sodium or potassium carbonate.

The compound of formula (XII) may be prepared by the reaction of glyoxylic acid with the compounds of the formula (XIII) as hereinbefore defined.

The compound of the formula (XIII) where $R_2$ is not hydrogen may be prepared by the reaction of the compound of the formula (XIV):

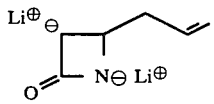
(XIV)

with a compound of the formula (XV) or (XVI):

$R_4.CO.R_5$ (XV)

$R_4(R_5)CHX$ (XVI)

wherein $R_4$ and $R_5$ are as defined in relation to formula (II) and X is a chlorine, bromine or iodine atom; and thereafter acylating the product formed by reaction with the compound of the formula (XV) if desired.

Generally the compound of the formula (XIV) is generated and utilized in situ. Thus 4-allyl-azetidin-2-one may be treated with two equivalents of n-butyl lithium in tetrahydrofuran at a low temperature. The dianion may be quenched by the addition of a compound of the formula (XV) or (XVI).

The esters of the compound of the formula (VIII) may also be prepared by the ozonolysis of an ester of a compound of the formula (XVII):

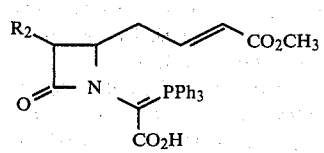
(XVII)

wherein $R_2$ is as defined in relation to formula (II) followed by m-chloroperbenzoic acid.

The ozonolysis is generally performed in the presence of trifluoroacetic acid in methylene chloride at $-70°$ C.

The ester of the compound of the formula (XVII) may be prepared via reaction of triphenylphosphine and the corresponding chloro compound which may in turn be prepared from the corresponding hydroxy compound which may be prepared from the N-H compound of the formula (XVIII):

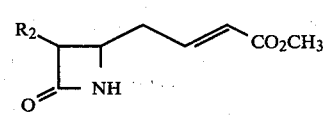
(XVIII)

wherein $R_2$ is as defined in relation to formula (II). This sequence may be carried out in analogous manner to the sequence (XIII)→(XII)→(XI)→(X) as hereinbefore described.

The compound of the formula (XVIII) may be prepared by the oxidation of a compound of the formula (XIX):

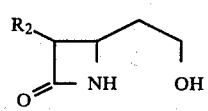
(XIX)

wherein $R_2$ is as defined in relation to formula (II) with pyridinium chlorochromate and thereafter reacting in situ the thus produced aldehyde of the formula (XX):

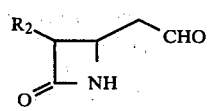
(XX)

with $Ph_3P=CHCO_2CH_3$.

The oxidation may be carried out in methylene chloride or the like at room temperature. When the oxidation is judged complete (for example by tlc) the reaction may be filtered and the phosphorane may be added to the filtrate for reaction.

The compound of the formula (XIX) may be prepared by the mild acid hydrolysis of a corresponding compound of the formula (XXI):

(XXI)

or the corresponding spirocyclohexyl analogue wherein $R_2$ is as defined in relation to formula (II).

The preceding hydrolysis may be carried out in aqueous acetone using small quantities of mineral or sulphuric acid.

Esters of the compound of the formula (X) may also be prepared by the reaction of an ester of a compound of the formula (XXII):

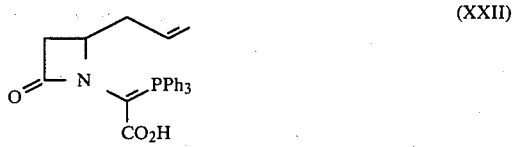

(XXII)

with a compound of the formula (XV) or (XVI) as hereinbefore defined in the presence of a strong base and thereafter if desired acylating the product formed by reaction with a compound of the formula (XV).

Strong bases for use in this reaction are those of low nucleophilicity such as lithium n-isopropylcyclohexylamide and similar reagents. The reaction is generally carried out in tetrahydrofuran at a low temperature such as $-80°$ C.

The compound of the formula (XXII) may be prepared from the corresponding chloro compound which in turn may be prepared from the corresponding hydroxy compound and that from the corresponding N-H compound by processes analogous to that for the sequence (XIII)→(XII)→(XI)→(X) as hereinbefore described.

Intermediates useful for the synthesis of compounds of this invention are described in:

European Patent Application Publication No. 0000828
British Cognate Application No. 11747/77–11749/77
French Application Publication No. 2392996
West German Application No. 2811514.2
Japanese Application No. 32804/78
United States Application Ser. No. 887,844
United States Application Ser. No. 887,841
Belgian Pat. No. 860962

The Description herein describe the preparation of typical examples of such intermediates.

The following Examples illustrate the invention:

DESCRIPTION 1

Preparation of 4-allyl-1-(1-phthalidyloxycarbonyl-1-triphenylphosphoranylidenemethyl)azetidin-2-one Allylazetidinone (6.3 g), glyoxylic acid monohydrate (5.52 g), 30 4 Å molecular sieves (⅛″ pellets) and dry dimethylformamide (30 ml) were stirred for 4 hours at room temperature. The mixture was cooled to 0° C. and finely powdered potassium carbonate (4.14 g) was added. The mixture was allowed to warm to room temperature and was stirred for 15 minutes. The solution was again cooled to 0° C. and bromophthalide (12.8 g) was added. The resulting solution was stirred for 2½ hours at room temperature and then poured onto $N/10$ hydrochloric acid (250 ml) and ethyl acetate (250 ml). The organic extract was washed once more with $N/10$ hydrochloric acid (250 ml) and then with half saturated sodium hydrogen carbonate (250 ml) and brine (250 ml), each aqueous washing being extracted once with ethyl acetate (100 ml). The combined organic extracts were dried ($Na_2SO_4$) and the solvent removed under reduced pressure to give an oil.

A stirred solution of this oil in dry tetrahydrofuran (250 ml), under argon, was cooled to $-20°$ C., and treated with 2,6-lutidine (7.6 ml) followed by thionyl chloride (4.8 ml) in tetrahydrofuran (30 ml). After stirring for 20 minutes at $-20°$ C. the mixture was brought to room temperature and filtered. The precipitate solid was washed with toluene and the combined filtrate and washings were evaporated to a small volume under reduced pressure. The residue was dissolved in toluene and re-evaporated to dryness twice to remove excess thionyl chloride.

The oil obtained was dissolved in dry tetrahydrofuran (250 ml) and treated with 2,6-lutidine (7.6 ml) and triphenylphosphine (12 g). After stirring for 16 hours, the mixture was filtered and the solvent removed from the filtrate under reduced pressure. The filtrant was dissolved up in ethyl acetate (250 ml) and $N/10$ hydrochloric acid (250 ml) and added to the evaporated filtrate. The organic layer was separated and washed with $N/10$ hydrochloric acid (250 ml), water (250 ml), half-saturated sodium hydrogen carbonate (250 ml) and brine (250 ml); each aqueous extract being extracted with ethyl acetate (250 ml). The combined organic extracts were dried ($Na_2SO_4$), and the solvent removed under reduced pressure. Chromatography on silica eluting with 1:1 ethyl acetate-pet. ether grading to ethyl acetate gave the title compound (8 g) as a foam which crystallised on addition of ether; (6 g) m.p. 182°–195° (ethyl acetate-pet. ether) (Found: C, 72.8; N, 5.0; H, 2.5%, $C_{34}H_{28}NO_5P$ requires C, 72.7; H, 5.0; N, 2.5%).

DESCRIPTION 2

Preparation of 1-(1-phthalidyloxycarbonyl-1-triphenylphosphoranylidenemethyl)-4-carboxymethylazetidin-2-one Part of the title compound from description 1 (1.68 g) was dissolved in a solution of trifluoroacetic acid (18 ml) in dry methylene chloride (90 ml) and left for 10 minutes at room temperature. The mixture was cooled to $-40°$ C. and ozone passed through the solution with stirring until blue (n.b. trifluoroacetic acid precipitates out of solution so care should be taken to ensure good mixing). Excess ozone was removed by passing argon through the solution at $-40°$ and a solution of m-chloroperbenzoic acid (0.51 g) in methylene chloride (15 ml) was added. The mixture was allowed to reach room temperature slowly and then stirred overnight. The solution was diluted with toluene (50 ml) and was reduced in volume to 50 ml in vacuo. Excess trifluoroacetic acid was removed by azeotroping twice with toluene (75 ml) and the residue was dissolved in ethyl acetate and chloroform. Chromatography of this solution on silica eluting with chloroform-ethyl acetate mixtures gave the title compound (1.08 g) as a light yellow solid. Recrystallisation from chloroform-pet. ether gave pure acid m.p. 176°–80° having $\nu_{max}$ (CHCl$_3$) 3000, 1780, 1740, 1615 and 980 cm$^{-1}$.

EXAMPLE 1

Benzyl 3-(2-pyrimidylthio)-7-oxo-1-azabicyclo[3.2.0]hept-2-ene-2-carboxylate

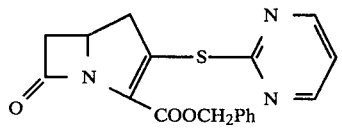

(i) Preparation of 1-(1-benzyloxycarbonyl-1-triphenylphos-phoranylidenemethyl)-4-(2-pyrimidylthiocarbonylmethyl)azetidin-2-one

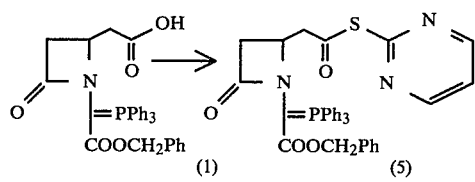

To the phosphorane acid (1) (0.8 g) in dry tetrahydrofuran (30 ml) was added in turn triethylamine (0.32 ml) and diethyl chlorophosphate (0.4 g) in tetrahydrofuran (3 ml). The mixture was stirred for 3 hours at room temperature in an inert atmosphere. Thallium 2-pyrimidylthiolate (1.0 g) (prepared from 2-mercaptopyrimidine and thallous ethoxide in ethanol) was added and the reaction mixture was stirred for 16 hours. The residue obtained after filtration and removal of solvent was dissolved in ethyl acetate (50 ml) and washed with aqueous sodium bicarbonate solution, water, and brine; each aqueous layer being washed once with ethyl acetate (30 ml). The combined organic extracts were dried (MgSO$_4$) and the solvent removed under reduced pressure. Chromatography on silica eluting with pet. ether-ethyl acetate mixtures followed by chromatography on florisil eluting with ethyl acetate gave the phosphorane (5) (0.3 g) m.p. 136°–139° (ex. ethylacetate-pet. ether) having $\nu_{max}$ (CHCl$_3$) 3000, 1740, 1720 sh, 1620, 1385 and 1105 cm$^{-1}$ (Found C, 68.2; H, 4.8; N, 6.75; S, 5.00. C$_{36}$H$_{30}$N$_3$O$_4$PS requires C, 68.5; H, 4.75; N, 6.65; S, 5.05%).

(ii) Preparation of benzyl 3-(2-pyrimidylthio)-7-oxo-1-azabicyclo[3.2.0]hept-2-ene-2-carboxylate

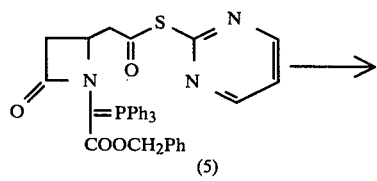

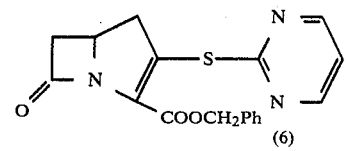

The phosphorane (5) (0.05 g) was dissolved in dry toluene (60 ml) and the solution was degassed under low vacuum. The solution was then heated at reflux under argon for 2 hours. Removal of solvent and chromatography on florisil eluting with 7:3 ethyl acetate-pet. ether gave the product (6) (0.02 g) having $\lambda_{max}$ (EtOH) 212, 244 and 317 nm; $\nu_{max}$ (CHCl$_3$) 3000, 1790, 1720, 1565, 1380, 1275 and 1185 cm$^{-1}$; $\delta$(CDCl$_3$) 2.95 (1H, dd, J3, 17 Hz, C6-H$_A$), 3.15 (1H, dd, J9, 18 Hz, C4-H$_A$), 3.47 (1H, dd, J6, 17 Hz, C6-H$_B$), 3.85 (1H, dd, J9, 18 Hz, C4-H$_B$), 4.28 (1H, ddt, J3, 6, 9 Hz, C5-H), 5.28 (2H, s, CH$_2$Ph), 7.03 (1H, t, J 5 Hz, pyrimidyl C4-H), 7.34 (5H, m, Ph), and 8.53 (2H, d, J 5 Hz, pyrimidyl C3 and C5-H).

The minimum inhibitory concentration of this compound to inhibit the growth of the following bacteria are:

| Organisims | μg/ml |
|---|---|
| | (agar + 10% horse blood) |
| *Citrobacter freundii* E8 | 5.0 |
| *Enterobacter cloacae* N1 | 25 |
| *Escherichia coli* 0111 | 5.0 |
| *Escherichia coli* JT39 | 50 |
| *Klebsiella aerogenes* A | 2.5 |
| *Proteus mirabilis* C977 | 25 |
| *Proteus morganii* 1580 | 50 |
| *Salmonella typhimurium* CT10 | 10 |
| *Serratia marcescens* US20 | 50 |
| *Shigella sonnei* MB 11967 | 10 |
| *Bacillus subtilis* A | 1.0 |
| *Staphylococcus aureus* Oxford | 2.5 |
| *Staphylococcus aureus* Russell | 10 |
| *Staphylococcus aureus* 1517 | 100 |
| *Streptococcus pyogenes* CN10 | 0.1 |

EXAMPLE 2 p-Nitrobenzyl 3-(2-pyrimidylthio)-7-oxo-1-azabicyclo[3.2.0.]hept-2-ene-2-carboxylate

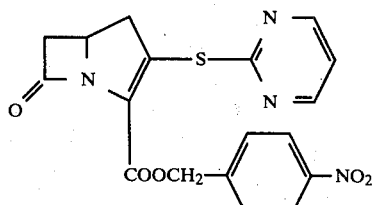

(ii) Preparation of 1-(1-p-nitrobenzyloxycarbonyl-1-triphenylphos-phoranylidenemethyl)-4-(2-pyrimidylthiocarbonylmethyl)azetidin-2-one

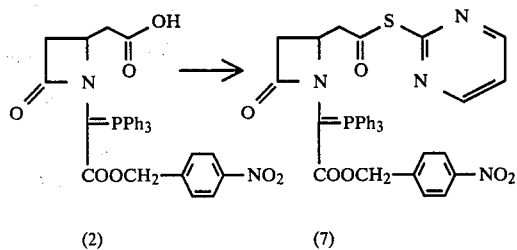

To the phosphorane acid (2) (1.25 g) in dry acetonitrile (30 ml) was added thionyl chloride (0.16 ml). After stirring for 3 hours at room temperature in an inert atmosphere, triethylamine (0.49 ml) was added followed by sodium 2-pyrimidylthiolate (prepared from 2-mercaptopyrimidine and sodium ethoxide). The mixture was stirred vigorously for one hour and then the solvent was removed under reduced pressure. The residue was dissolved in ethyl acetate (100 ml) and washed in turn with water (100 ml), saturated sodium bicarbonate (100 ml) and brine (50 ml); each aqueous washing being extracted once more with ethyl acetate (50 ml). The combined organic extracts were dried (MgSO$_4$) and the solvent removed under reduced pressure. Chromatography on florisil eluting with ethyl acetate gave the phosphorane (7) as a light yellow needles (0.65 g) m.p. 150°–5° (ex. ethyl acetate-ether) having $v_{max}$ (CHCl$_3$) 3000, 1745, 1720sh, 1620, 1385 and 1350 cm$^{-1}$ (Found: C, 63.9; H, 4.25; N, 8.3; S, 5.1. C$_{36}$H$_{29}$N$_4$O$_6$PS requires C, 63.9; H, 4.3; N, 8.3; S, 4.75%).

(ii) Preparation of 1-(1-p-nitrobenzyloxycarbonyl-1-triphenylphos-phoranylidenemethyl)-4-(2-pyrimidylthiocarbonylmethyl)azetidin-2-one

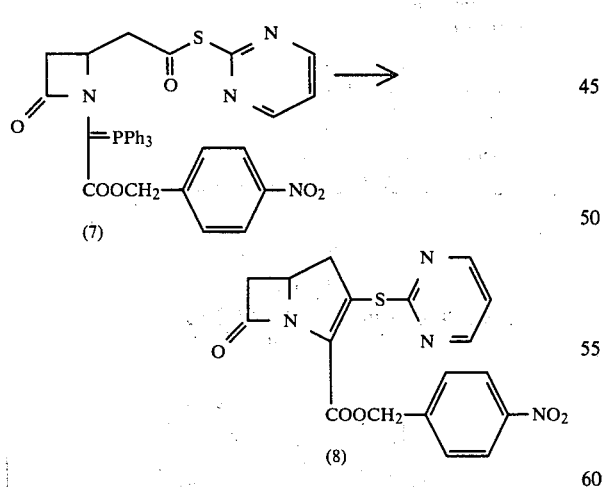

The phosphorane (7) (0.055 g) was dissolved in dry toluene (70 ml) and the solution was degassed under low vacuum. The solution was then heated under reflux for 3½ hours under argon. Removal of solvent and chromatography on florisil eluting with 7:3 ethyl acetate-pet. ether gave the product (8) (0.026 g) as needles m.p. 154°–160° (ex. ethyl acetate-ether) having $\lambda_{max}$ (EtOH) 320 and 265 nm; $v_{max}$ (CHCl$_3$) 3040, 3010, 1790, 1720, 1610, 1560, 1525, 1380 and 1350 cm$^{-1}$; δ(CDCl$_3$) 3.01 (1H, dd, J 4, 16 Hz, C6-H$_A$), 3.17 (1H, dd, J 9, 17 Hz, C4-H$_A$), 3.54 (1H, dd, J 6, 16 Hz, C6-H$_B$), 3.81 (1H, dd, J 9, 17 Hz, C4-H$_B$), 4.33 (1H, ddt, J 4, 6, 9 Hz, C5-H), 5.28 (1H, d, J 14 Hz, OC$\underline{H}_A$H$_B$Ar), 5.51 (1H, d, J 14 Hz, OCH$_A$$\underline{H}_B$Ar), 7.09 (1H, t, J 6 Hz, pyrimidyl C5-H), 7.64 (2H, d, J 9 Hz, ArNO$_2$), 8.21 (2H, d, J 9 Hz, ArNO$_2$), and 8156 (2H, d, J 6 Hz, pyrimidyl C4-and C6-H) (Found: C, 54.7; H, 3.2; N, 14.1 C$_{18}$H$_{14}$N$_4$O$_5$S requires C, 54.3; H, 3.5; N, 14.1%).

The minimum inhibitory concentrations of this compound to inhibit the growth of the following bacteria are:

| Organisms | μg/ml |
|---|---|
| | (agar + 10% horse blood) |
| *Citrobacter freundii* C8 | 10 |
| *Enterobacter cloacae* N1 | 50 |
| *Escherichia coli* 0111 | 5.0 |
| *Escherichia coli* JT39 | 25 |
| *Klebsiella aerogenes* A | 5.0 |
| *Proteus mirabilis* C977 | 25 |
| *Proteus morganii* I580 | 10 |
| *Proteus rettgeri* WM16 | 50 |
| *Proteus vulgaris* WO91 | 50 |
| *Pseudomonas aeruginosa* A | 50 |
| *Salmonella typhimurium* CT10 | 10 |
| *Serratia marcescens* US20 | 25 |
| *Shigella sonnei* MB 11967 | 5.0 |
| *Bacillus subtilis* A | 2.5 |
| *Staphylococcus aureus* Oxford | 5.0 |
| *Staphylococcus aureus* Russell | 5.0 |
| *Staphylococcus aureus* 1517 | 50 |
| *Streptococcus faecalis* I | 50 |
| *Streptococcus pyrogenes* CN10 | 2.5 |

EXAMPLE 3

Phthalidyl 3-(4,6-dimethyl-2-pyrimidylthio)-7-oxo-1-azabicyclo[3.2.0]hept-2-ene-2-carboxylate

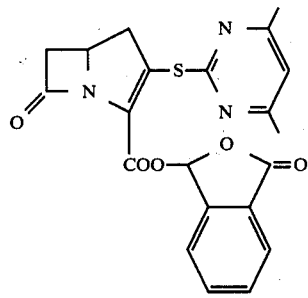

(i) Preparation of 1-(1-phthalidyloxycarbonyl-1-triphenylphosphoranylidenemethyl)-4-(4,6-dimethyl-2-pyrimidylthiocarbonylmethyl)azetidin-2-one

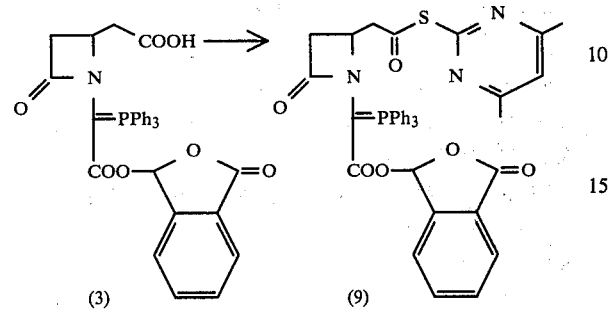

To the phosphorane acid (3) (0.3 g) in dry tetrahydrofuran (15 ml) was added in turn triethylamine (0.11 ml) and diethyl chlorophosphate (0.13 g) in tetrahydrofuran (2 ml). The mixture was stirred for 3 hours at room temperature in an inert atmosphere. Lithium 4,6-dimethyl-2-pyrimidylthiolate (0.075 g) (prepared from lithium ethoxide and 4,6-dimethyl-2-pyrimidylthiol) was added and the mixture stirred for 1¾ hours. The solvent was removed under reduced pressure and the residue dissolved in a mixture of ethyl acetate (25 ml) and water (20 ml). The organic layer was washed with half saturated sodium hydrogen carbonate (2×20 ml) and brine (20 ml); each aqueous washing being extracted once with ethyl acetate (20 ml). The combined organic extracts were dried (Na$_2$SO$_4$) and the residue, after evaporation of solvent, was chromatographed on a small florisil column eluting with ethyl acetate. The fractions containing the product were combined and reduced in volume to about 5 ml. Pet ether was added and the phosphorane (9) (0.2 g) crystallised m.p. 122–130 (ethylacetate-pet. ether) having $\nu_{max}$ (CHCl$_3$), 3000, 1780, 1745, 1665, and 1590 cm$^{-1}$ (Found C, 65.2; H, 4.95; N, 5.30. C$_{39}$H$_{32}$N$_3$O$_6$PS. H$_2$O requires C, 65.1; H, 4.75; N, 5.85%).

(ii) Preparation of phthalidyl 3-(4,6-dimethyl-2-pyrimidylthio)-7-oxo-1-azabicyclo[3.2.0]hept-2-ene-2-carboxylate

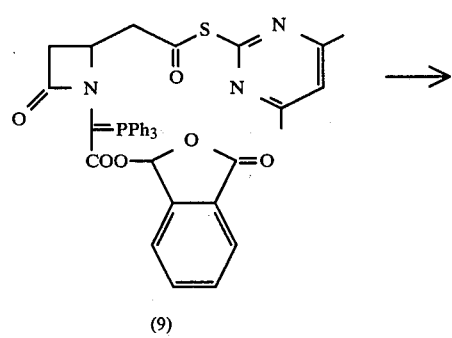

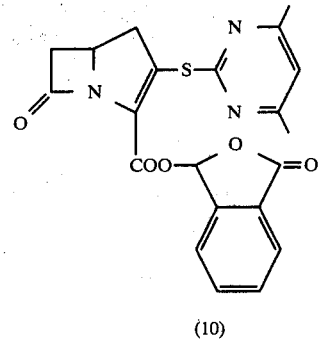

The phosphorane (9) (0.084 g) was dissolved in dry toluene (150 ml) and the solution was degassed under low vacuum. The solution was then heated under reflux for 3 hours under argon. Removal of solvent and chromatography on silica eluting with ethyl acetate gave the product (10)(0.012 g) as off-white crystals (ex. ethyl acetate) having $\lambda_{max}$ (ethyl acetate) 326 nm; $\nu_{max}$ (CHCl$_3$) 3000, 1790, 1730, 1660, 1585, 1260 and 980 cm$^{-1}$; $\delta$(CDCl$_3$) 2.43 (6H, s, CH$_3$), 2.96 (1H, dd, J 3, 17 Hz, C6-H$_A$), 3.11 (1H, dd, J 9, 18 Hz, C4-H$_A$), 3.50 (1H, dd, J 5, 17 Hz, C6-H$_B$), 3.82 (1H, dd, J 10, 18 Hz, C4-H$_B$), 4.22 (1H, m, C5-H), 6.78 (1H, s, pyrimidyl C5-H), 7.46 and 7.51 (1H, 2×s∼1:4, 2 isomeric phthalide methine H), and 7.55–7.95 (4H, m, phthalide aromatic) (M+, 423.0861. C$_{21}$H$_{17}$N$_3$O$_5$S requires M, 423.0889).

The minimum inhibitory concentrations of this compound to inhibit the growth of the following bacteria are given below.

| Organisms | µg/ml |
| --- | --- |
|  | (D.S.T. agar + 10% horse blood) |
| *Escherichia coli* 0111 | 12.5 |
| *Escherichia coli* ESS | 2.5 |
| *Escherichia coli* JT 39 |  |
| *Klebsiella aerogenes* A | 12.5 |
| *Proteus mirabilis* C977 | 25 |
| *Pseudomonas aeruginosa* A |  |
| *Salmonella typhimurium* CT10 | 50 |
| *Bacillus subtilis* A | 12.5 |
| *Staphylococcus aureus* Oxford | 25 |
| *Staphylococcus aureus* Russell | 25 |
| *Streptococcus pyrogenes* CN10 | 0.5 |

EXAMPLE 4

Phthalidyl 3-(2-pyrimidylthio)-7-oxo-1-azabicyclo[3.2.0]hept-2-ene-2-carboxylate

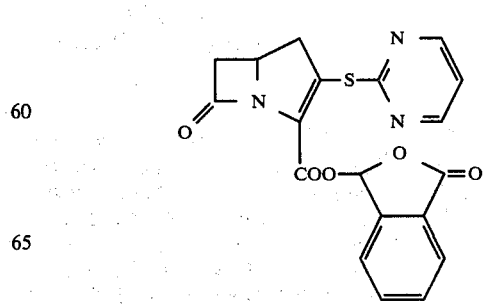

(i) Preparation of 1(1-phthalidyloxycarbonyl-1-triphenylphosphoranylidenemethyl)-4-(2-pyrimidylthiocarbonylmethyl)azetidin-2-one

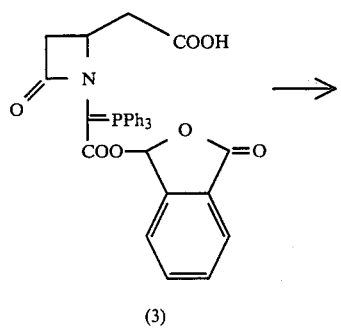

(3)

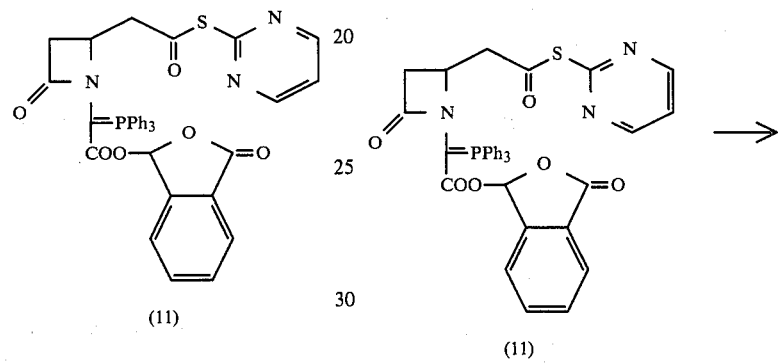

(11)

(a) Using sodium pyrimidylthiolate

To the phosphorane acid (3) (0.29 g) in dry tetrahydrofuran (15 ml) was added in turn triethylamine (0.105 ml) and diethyl chlorophosphate (0.13 g) in tetrahydrofuran (2 ml). The mixture was stirred for 3 hours at room temperature in an inert atmosphere. Sodium 2-pyrimidylthiolate (0.07 g) (prepared from sodium ethoxide and 2-pyrimidylthiol) was added and the mixture stirred for 1 hour. The solvent was removed under reduced pressure and the residue was dissolved in a mixture of ethyl acetate (25 ml) and water (20 ml). The organic layer was washed with half saturated sodium hydrogen carbonate (20 ml) and brine (20 ml); each aqueous extract being extracted once with ethyl acetate (20 ml). The combined organic extracts were dried (Na2SO4) and the residue, after evaporation of solvent, was chromatographed on a small florisil column eluting with 1:1 pet. etherethylacetate grading to ethyl acetate. The product was obtained as an oil which crystallised on addition of ether to give the thioester (11) (0.105 g) as pale yellow needles m.p. 136°-142° (ethylacetate pet. ether) having $\nu_{max}$ (CHCl3) 3000, 1775, 1745, 1665, 1555, 1385 and 955 cm$^{-1}$ (Found: C, 63.5; H, 4.30; N, 6.20. C37H28N3O6PS 1½% H2O requires C, 63.4; H, 4.45; N, 6.00%).

(b) Using lithium pyrimidylthiolate

To the phosphorane acid (3) (0.48 g) in dry tetrahydrofuran (30 ml) was added in turn triethylamine (0.17 ml) and diethyl chlorophosphate (0.21 g) in tetrahydrofuran (2 ml). The mixture was stirred for 3 hours at room temperature in an inert atmosphere. Lithium 2-pyrimidylthiolate (4 ml of a freshly prepared 0.2 m molar solution of lithium 2-pyrimidylthiolate, prepared in turn from lithium ethoxide and the thiol, in dry tetrahydrofuran) was added and the mixture stirred for 2½ hours. The solvent was removed under vacuum and the residue was dissolved in a mixture of ethyl acetate (30 ml) and water (20 ml). The organic layer was extracted with saturated sodium hydrogen carbonate solution (25 ml) and brine (20 ml); each aqueous extract being extracted once with ethyl acetate (20 ml). The combined organic extracts were dried (Na2SO4) and the residue, after evaporation of solvent, was chromatographed on florisil eluting with ethyl acetate. The fractions containing the product were combined and reduced in volume to about 5 ml. Pet. ether was added and the thioester (11) (0.22 g) crystallised. This product was identical with that obtained in Example 4 (i) (a).

(ii) Preparation of phthalidyl 3-(2-pyrimidylthio)-7-oxo-1-azabicyclo[3.2.0]hept-2-ene-2-carboxylate

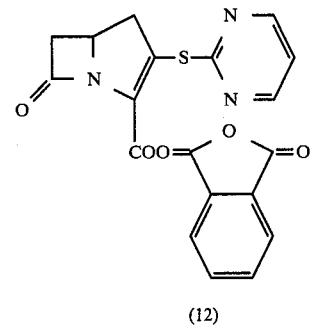

(12)

The phosphorane (11) (0.095 g) was dissolved in dry toluene (120 ml) and the solution was degassed under low vacuum. The solution was then heated under reflux for 3¼ hours under argon. Removal of solvent and chromatography on silica eluting with ethyl acetate gave the product (12) (0.014 g) as an oil. Recrystallisation from ethyl acetate-pet. ether gave the product (12) (0.008 g) as off-white needles, $\lambda_{max}$ (ethylacetate) 325 nm; $\nu_{max}$ (CHCl3) 2960, 1790, 1730, 1560, 1380 and 980 cm$^{-1}$; δ(CDCl3) 2.85–4.05 (4H, C4 and C6 methylenes) including 3.02 (dd, J 3, 17 Hz, C6-H) and 3.83 (dd, J 10, 17 Hz, C4-H), 4.27 (1H, m, C5-H), 7.08 and 7.11 (1H, 2xt, J 5 Hz, pyrimidyl C5-H in 2 phthalidyl ester diastereoisomers), 7.48 and 7.52 (1H, 2×s, 2 phthalidyl methines), 7.70 (4H, m, phthalide aromatics), and 8.56 and 8.59 (2H, 2×d, J 5 Hz, pyrimidyl C4- and C6-H in 2 phthalidyl ester diastereoisomers) (M+, 395.0581. C19H13N3O5S requires M, 395.0576).

The minimum inhibitory concentrations of this compound to inhibit the growth of the following bacteria are given below:

| Organisms | µg/ml |
|---|---|
| | (agar + 10% horse blood) |
| *Escherichia coli* ESS | 1.2 |
| *Escherichia coli* 0111 | 12.5 |
| *Escherichia coli* JT39 | |
| *Klebsiella aerogenes* A | 12.5 |
| *Proteus mirabilis* C977 | |
| *Pseudomonas Aeruginosa* A | |
| *Salmonella typhimurium* CT10 | 25 |
| *Shigella sonnei* MB 11967 | 25 |
| *Bacillus subtilis* A | 1.2 |
| *Staphylococcus aureus* Oxford | 12.5 |
| *Staphylococcus aureus* Russell | 25 |
| *Streptococcus pneumoniae* CN33 | 0.5 |
| *Streptococcus pyogenes* CN10 | 1.2 |

EXAMPLE 5

Benzyl 3-(4,6-dimethyl-2-pyrimidylthio)-7-oxo-1-azabicyclo[3.2.0]hept-2-ene-2-carboxylate

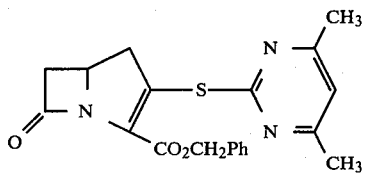

(i) Preparation of 1-(1-benzyloxycarbonyl-1-triphenylphosphoranylidenemethyl)-4-(4,6-dimethyl-2-pyrimidylthiocarbonylmethyl)azetidin-2-one

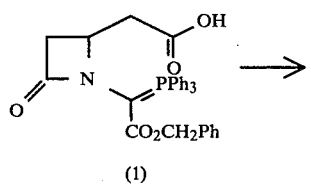
(1)

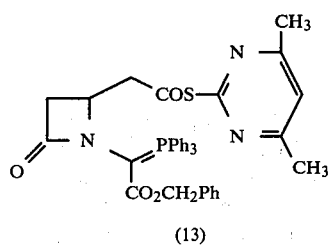
(13)

The phosphorane acid (1) (1.072 g) was dissolved in tetrahydrofuran (30 ml) and treated with triethylamine (0.202 g) followed by diethyl phosphorochloridate (0.38 g). The reaction was stirred at room temperature for 2 hours and treated with lithium 4,6-dimethyl-2-pyrimidylthiolate (0.3 g) (prepared by adding the thiol to a solution of lithium in ethanol and evaporating the solid from toluene). The reaction was stirred at room temperature for one hour, the solvent evaporated and the residue chromatographed on florisil using ethyl acetate as eluant. The fractions containing the product were combined and washed with saturated sodium bicarbonate solution (3×25 ml), dried (MgSO₄) and evaporated to yield a gum which was covered with ether and left at 0° overnight. Trituration gave the thioester phosphorane (13) as a white crystalline solid (0.95 g; 72%) m.p. 165°–6°, $\nu_{max}$ (CHCl₃) 1740, 1610, 1585, 1435, 1105 cm$^{-1}$ (Found: C, 69.17; H, 5.26; N, 6.25. $C_{38}H_{34}N_3O_4SP$ requires C, 69.29; H, 5.16; N, 6.37%).

(ii) Preparation of benzyl-3-(4,6-dimethyl-2-pyrimidylthio)-7-oxo-1-azabicyclo[3.2.0]hept-2-ene-2-carboxylate

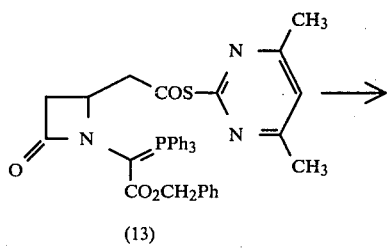
(13)

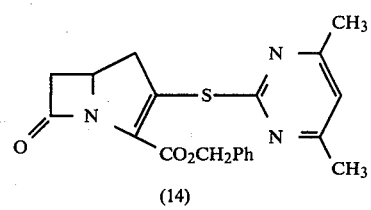
(14)

The thioester phosphorane (13) (0.5 g) was dissolved in dry toluene (500 ml) and refluxed vigorously under argon for 3 hours. The solvent was evaporated and the residue chromatographed on silica H to yield the product (14) as a white crystalline solid from ether (0.185 g) m.p. 128°–30°, $\lambda_{max}$ (EtOH) 317 nm ($\epsilon$14000); $\nu_{max}$ (CHCl₃) 1785, 1710, 1595, 1265 cm$^{-1}$; δppm (CDCl₃) 2.35 (6H, s, CH₃'s), 2.90 (1H, dd, J 17, 3 Hz, C6-Ha), 3.05 (1H, dd, J 17, 9 Hz, C4-Ha), 3.44 (1H, dd, J 17, 5.5 Hz, C6-Hb), 3.72 (1H, dd, J 17, 9 Hz, C4-Hb), 4.20 (1H, m, C5-H), 5.25 (2H, s, benzyl CH₂), 6.71 (1H, s, pyrimidyl CH), 7.10–7.50 (5H, m, Ar) (Found: C, 63.16; H, 5.09; N, 10.92. M⁺, 381.1139. $C_{20}H_{19}N_3O_3S$ requires C, 62.9; H, 4.99; N, 11.02%; M, 381.1147).

The minimum inhibitory concentrations of this compound required to hinhibit the growth of the following bacteria are given below:

| Organisms | µg/ml |
|---|---|
| | (D.S.T. agar + 10% Horse Blood) |
| *Citrobacter freundii* | 12.5 |
| *Escherichia coli* 0111 | 50 |
| *Klebsiella Aerogenes* A | 50 |
| *Staphylococcus aureus* Oxford | 50 |
| *Streptococcus pneumoniae* CN33 | 2.5 |
| *Streptococcus pyogenes* CN10 | 2.5 |
| *Escherichia coli* ESS | 12.5 |

EXAMPLE 6 p-Nitrobenzyl 3-(4,6-dimethyl-2-pyrimidylthio)-7-oxo-1-azabicyclo[3.2.0]hept-2-ene-2-carboxylate

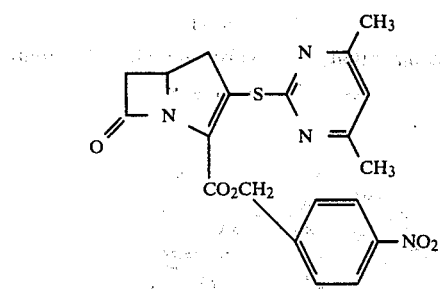

(i) Preparation of 1-(1-p-nitrobenzyloxycarbonyl-1-triphenylphoranylidenemethyl)-4-(4,6-dimethyl-2-pyrimidylthiocarbonylmethyl)azetidin-2-one

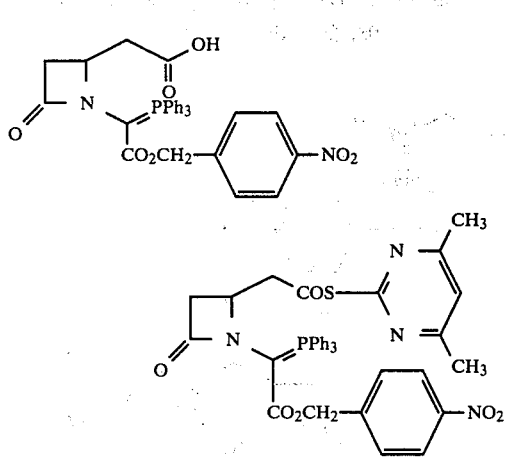

The phosphorane acid (2) (1.164 g) was dissolved in tetrahydrofuran (30 ml) and treated with triethylamine (0.202 g) followed by diethyl phosphorochloridate (0.38 g) in tetrahydrofuran (5 ml). The reaction was stirred at room temperature for 3 hours and treated with lithium 4,6-dimethyl-2-pyrimidylthiolate (0.3 g). The reaction was stirred at room temperature for a further hour, the solvent evaporated and the crude product chromatographed on silica H using ethyl acetate as eluant. The collected ethyl acetate fractions containing the product were washed with saturated sodium bicarbonate solution (3×25 ml) and dried (MgSO₄). The solvent was evaporated and the residue crystallised when under ether at 0° overnight to give the product (15) as a white solid (0.98 g; 70%) m.p. 157°-60°, $\nu_{max}$ (CHCl₃) 1735, 1620, 1585, 1520, 1435, 1345 cm⁻¹ (Found: C, 64.38; H, 4.99; N, 7.88. C₃₈H₃₃N₄O₆SP requires C, 64.77; H, 4.68; N, 7.95%).

(ii) Preparation of p-nitrobenzyl-3-(4,6-dimethyl-2-pyrimidylthio)-7-oxo-1-azabicyclo[3.2.0]hept-2-ene-2-carboxylate

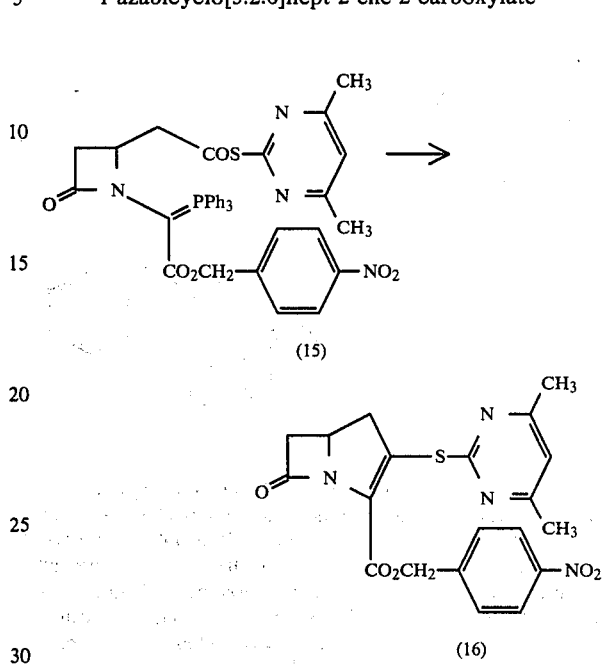

The thioester phosphorane (15) (0.7 g) was dissolved in dry toluene (1300 ml) and refluxed for 3 hours. The solvent was evaporated and the residue chromatographed on silica H to yield (16) as a white crystalline solid from ether m.p. 160°-4°, $\nu_{max}$ (EtOH) 263 nm (ε14800) 319 nm (ε14800); $\nu_{max}$ (CHCl₃) 1780, 1715, 1585, 1525 cm⁻¹; δppm (CDCl₃) 2.45 (6H, s, CH₃'s) 3.00 (1H, dd, J 3, 16 Hz, C6-H$_A$), 3.20 (1H, dd, J 9, 17 Hz, C4-H$_A$), 3.56 (1H, dd, J6, 16 Hz, C6-H$_B$) 3.86 (1H, dd, J 9, 17 Hz, C4-H$_B$), 4.28 (1H, m, C5-H), 5.29 and 5.53 (2H, ABq, J 14 Hz, benzyl-CH₂), 6.83 (1H, s, pyrimidyl C4-H) 7.67 (2H, d, J 9 Hz, ArNO₂), 8.24 (2H, d, J 9 Hz, ArNO₂) (Found: C, 56.09; H, 4.04; N, 12.73; M⁺426.1006; C₂₀H₁₈N₄OS requires C, 56.34; H, 4.23; N, 13.15%; M, 426.0996).

EXAMPLE 7

Benzyl 3-(4-pyrimidylthio)-7-oxo-1-azabicyclo[3.2.0]hept-2-ene-2-carboxylate

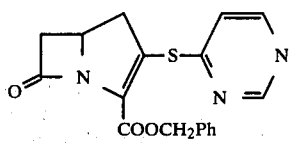

(i) Preparation of 1-(1-benzyloxycarbonyl-1-triphenylphosphoranylidenemethyl)-4-(4-pyrimidylthiocarbonylmethyl)azetidin-2-one

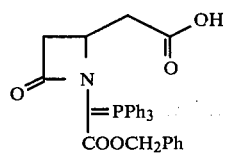

(1)

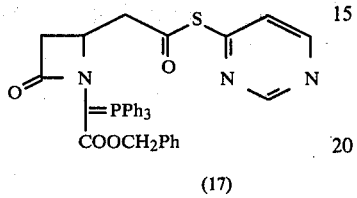

(17)

To the phosphorane acid (1) (0.535 g) in dry tetrahydrofuran (20 ml) was added in turn triethylamine (0.21 ml) and diethyl chlorophosphate (0.26 g) in tetrahydrofuran (2 ml). The mixture was stirred for 3 hours at room temperature in an inert atmosphere. Sodium 4-pyrimidylthiolate (0.135 g) (prepared from sodium ethoxide and 4-pyrimidylthiol) was added and the mixture stirred for 1 hour. The solvent was removed under reduced pressure and the residue dissolved in a mixture of ethyl acetate (40 ml) and water (30 ml). The organic layer was washed with saturated sodium hydrogen carbonate (30 ml) and brine (20 ml); each aqueous extract being extracted once with ethyl acetate (20 ml). The combined organic extracts were dried (Na$_2$SO$_4$) and the residue, after evaporation of solvent, was chromatographed on a small florisil column eluting with 1:1 pet. ether-ethyl acetate→ethyl acetate. This gave the thioester (17) an oil which crystallised from ethyl acetate-pet. ether m.p. 122°-7°, $\nu_{max}$ (CHCl$_3$) 3000, 1745, 1720 sh, 1620 and 1555 cm$^{-1}$ (Found: C, 68.05; H, 4.85; N, 6.50. C$_{36}$H$_{30}$N$_3$O$_4$PS requires C, 68.45; H, 4.75; N, 6.65%).

(ii) Preparation of benzyl 3-(4-pyrimidylthio)-7-oxo-1-azabicyclo[3.2.0]hept-2-ene-2-carboxylate

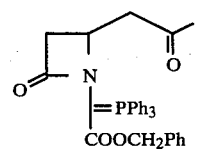

(17)

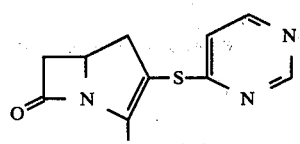

(18)

The phosphorane (17) (0.045 g) was dissolved in dry toluene (90 ml) and the solution was degassed under low vacuum. The solution was then heated at reflux in an inert atmosphere for 1 hour. Removal of solvent and chromatography on florisil eluting with pet. ether-ethyl acetate mixtures gave the product (18) as an impure oil having $\lambda_{max}$ (ethyl acetate) 325 nm; $\nu_{max}$ (CHCl$_3$) 3000, 1790, 1600, 1560 and 1380 cm$^{-1}$.

EXAMPLE 8 p-Nitrobenzyl 3-(4-pyrimidylthio)-7-oxo-1-azabicyclo[3.2.0]hept-2-ene-2-carboxylate

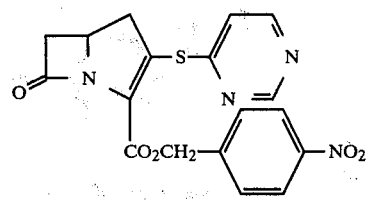

(i) Preparation of 1-(1-p-nitrobenzyloxycarbonyl-1-triphenylphosphoranylidenemethyl)-4-(4-pyrimidylthiocarbonylmethyl)azetidin-2-one

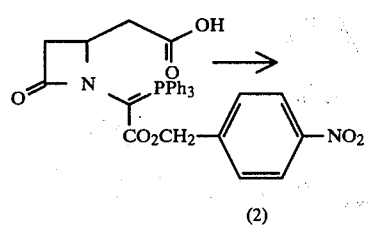

(2)

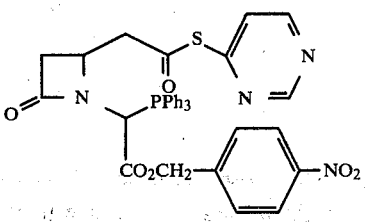

(19)

The phosphorane acid (2) (1.16 g) was dissolved in tetrahydrofuran (30 ml) and treated with triethylamine (0.202 g) followed by diethyl phosphorochloridate (0.38 g) and stirred at room temperature for 3 hours. Lithium-4-pyrimidylthiolate (0.25 g) in tetrahydrofuran (5 ml) was added and the mixture stirred at room temperature for one hour. Evaporation of the solvent and chromatography of the residue on silica H eluting with ethyl acetate gave the product (19) as a gum which solidified on trituration with ether after 2 days at 0° (0.5 g; 37%) m.p. 155°-6°, $\nu_{max}$ (CHCl$_3$) 1745, 1720 (sh), 1625, 1605, 1555, 1520, 1440, 1380, 1350 cm$^{-1}$ (Found: C, 63.71; H, 4.40; N, 8.03; C$_{36}$H$_{29}$N$_4$O$_6$SP requires C, 63.91; H, 4.29; N, 8.28%).

(ii) Preparation of p-nitrobenzyl 3-(4-pyrimidylthio)-7-oxo-1-azabicyclo[3.2.0]hept-2-ene-2-carboxylate

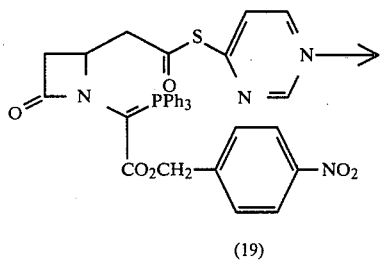

(19)

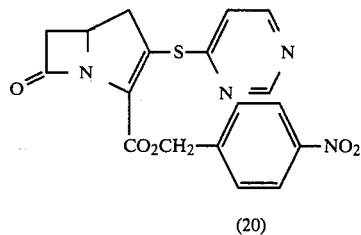

(20)

The thioester phosphorane (19) (0.15 g) was dissolved in dry toluene (150 ml) and heated under reflux for one hour under argon. Evaporation of the solvent and chromatography of the residue on silica H gave the product (20) as an oil contaminated with triphenylphosphine oxide (approx. 0.02 g), $\lambda_{max}$ (EtOH) 323 nm; $\nu_{max}$ (CHCl$_3$) 1785, 1725, 1560 cm$^{-1}$.

The minimum inhibitory concentrations of this compound required to inhibit the growth of the following bacteria are given below:

| Organisms | μg/ml (DST agar + 10% Horse Blood) |
|---|---|
| Enterobacter cloacae N1 | 5.0 |
| Escherichia coli 0111 | 12.5 |
| Klebsiella aerogenes | 5.0 |
| Proteus mirabilis C977 | 50 |
| Salmonella typhimurium CT10 | 5.0 |
| Shigella sonnei MB 11967 | 12.5 |
| Bacillus subtilis A | 5.0 |
| Staphylococcus aureus Oxford | 12.5 |
| Staphylococcus aureus Russell | 25.0 |
| Streptococcus pneumoniae CN33 | 0.5 |
| Streptococcus pyrogenes CN10 | 2.5 |
| E. coli ESS | 5.0 |

EXAMPLE 9

3-(2-Pyrimidylthio)-7-oxo-1-azabicyclo[3.2.0]hept-2-ene-2-carboxylate

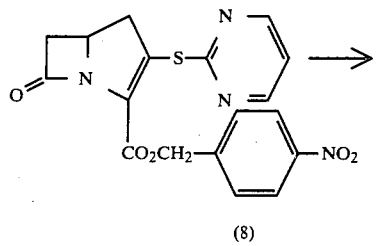

(8)

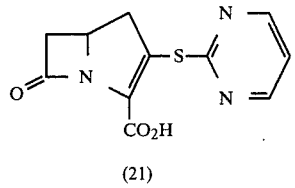

(21)

p-Nitrobenzyl-3-(2-pyrimidylthio)-7-oxo-1-azabicyclo[3.2.0]hept-2-ene-2-carboxylate (8) (0.075 g) was dissolved in dioxan (15 ml) and ethanol (0.75 ml) was added together with deionised water (2.5 ml) and $M/20$ phosphate buffer (3 ml). 10% Pd/C (0.09 g) was added and the mixture was hydrogenated at ambient temperature and pressure for 2 hours. The mixture was filtered through Kieselguhr and washed with water (10 ml). The filtrate was extracted with ether (3×10 ml) and evaporated to low volume (approx. 3 ml) and loaded onto an XAD-2 column. Elution with water gave the product (21) (0.008 g) in fractions 4–8 (5 ml fractions collected). Evaporation of the solution gave a white solid, $\lambda_{max}$ (H$_2$O) 294, 247 nm; $\nu_{max}$ (KBr) 1760, 1600, 1560, 1360 cm$^{-1}$.

EXAMPLE 10

3-(4,6-Dimethyl-2-pyrimidylthio)-7-oxo-1-azabicyclo[3.2.0]hept-2-ene-2-carboxylate

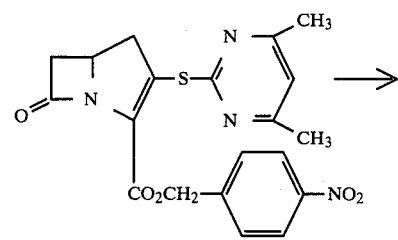

(16)

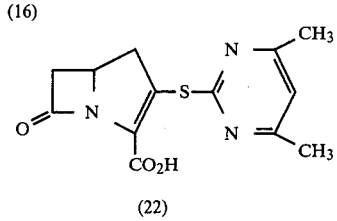

(22)

p-Nitrobenzyl-3-(4,6-dimethyl-2-pyrimidylthio)-7-oxo-1-azabicyclo[3.2.0]hept-2-ene-2-carboxylate (16) (0.075 g) was dissolved in dioxan (15 ml) and ethanol (0.75 ml), deionised water (2.5 ml) and $M/20$ phosphate buffer (3 ml) were added. 10% Pd/C (0.075 g) was added and the mixture was hydrogenated at ambient temperature and pressure for 2 hours. The mixture was filtered through Kieselguhr and more catalyst added (75 mg). The hydrogenolysis was continued for a further 2 hours. The mixture was filtered through Kieselguhr and washed with water (10 ml). The filtrate was extracted with ether (3×15 ml) and evaporated to low volume (approx. 3 ml), loaded onto an XAD-2 column and eluted with water. The product (22) was collected in fractions 3, 4 and 5 (10 ml fractions collected), $\lambda_{max}$ (H$_2$O) 297, 248 nm.

The minimum inhibitory concentrations of this compound required to inhibit the growth of the following bacteria are given below:

| Organisms | μg/ml (DST agar + 10% Horse Blood) |
|---|---|
| *Escherichia coli* 0111 | 5.0 |
| *Escherichia coli* ESS | 0.6 |
| *Klebsiella aerogenes* A | 5.0 |
| *Salmonella typhimurium* CT10 | 10.0 |
| *Shigella sonnei* MB 11967 | 10.0 |
| *Staphylococcus aureus* Oxford | 5.0 |
| *Streptococcus pyogenes* CN10 | <0.08 |

EXAMPLE 11 p-Nitrobenzyl 3-(4-methyl-2-pyrimidylthio)-7-oxo-1-azabicyclo[3.2.0]-hept-2-ene-2-carboxylate

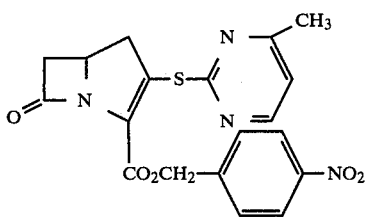

(i) Preparation of 1-(1-p-nitrobenzyloxycarbonyl-1-triphenylphosphoranylidenemethyl)-4-(4-methyl-2-pyrimidylthiocarbonylmethyl)azetidin-2-one

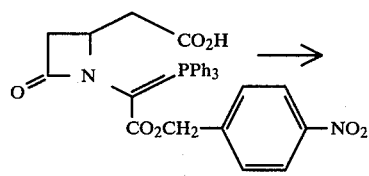

(2)

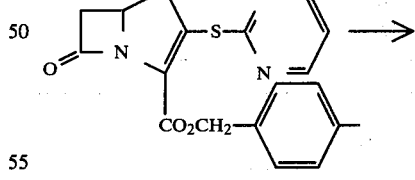

(23)

The title compound (23) was prepared as described in example 6 (i) in 25% yield as a white solid from ether mp. 114°–6°, $\nu_{max}$ (CHCl$_3$) 1735, 1620, 1605, 1750, 1520, 1345 cm$^{-1}$ (Found: C, 64.22; H, 4.39; N, 8.01 C$_{37}$H$_{31}$N$_4$O$_6$SP requires: C, 64.35; H, 4.49; N, 8.12%).

(ii) Preparation of p-nitrobenzyl-3-(4-methyl-2-pyrimidylthio)-7-oxo-1-azabicyclo[3.2.0]hept-2-ene-2-carboxylate

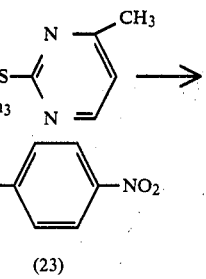

(23)

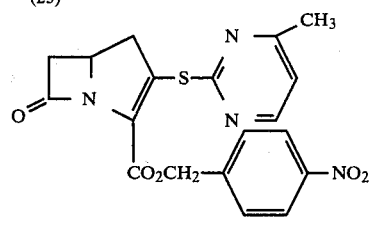

(24)

The thioester phosphorane (23) was cyclised as described in example 8(ii) to afford the title product (24) as a white solid from ether (50%) mp. 137°–40°, $\nu_{max}$ (EtOH) 263 nm (14,800) 319 nm (15,000); $\nu_{max}$ (CHCl$_3$) 1780, 1720, 1600, 1570, 1520, 1345, 1320 cm$^{-1}$; δ ppm [(CD$_3$)$_2$CO] 2.48 (3H, s, CH$_3$), 3.13 (1H, dd, J 3, 16 Hz, C6-H$_A$), 3.28 (1H, dd, J 9, 17 Hz, C4-H$_A$), 3.60 (1H, dd, J 6, 16 Hz, C6-H$_B$), 3.85 (1H, dd, J 9, 17 Hz, C4-H$_B$), 4.35 (1H, m, C5-H), 5.33 and 5.57 (2H, ABq, J 14 Hz, benzyl —CH$_2$), 7.18 (1H, d, J 5.5 Hz, pyrimidyl C5-H), 7.80 (2H, d, J 9 Hz, ArNO$_2$), 8.25 (2H, d, J 9 Hz, ArNO$_2$), 8.47 (1H, d, J 5.5 Hz, pyrimidyl C6-H) (Found C, 54.89; H, 3.79; N, 13.16. M+ 412.0815 C$_{19}$H$_{16}$N$_4$O$_5$S requires C, 55.33; H, 3.88; N, 13.59% M, 412.0841).

EXAMPLE 12

3-(4-Methyl-2-pyrimidylthio)-7-oxo-1-azabicyclo[3.2.0-]hept-2-ene-2-carboxylate

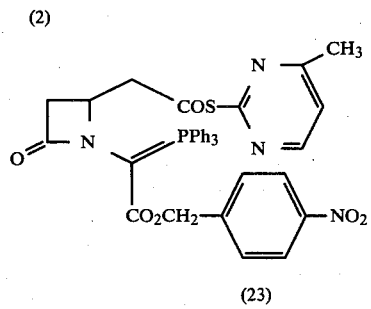

(24)

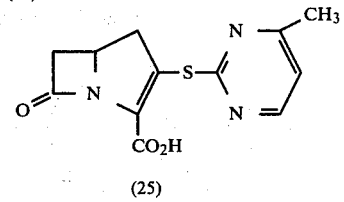

(25)

The p-nitrobenzyl ester (24) was deprotected as described in example 10 to provide the title product (25) (10%) $\lambda_{max}$ (H$_2$O) 297, 248 nm.

The minimum inhibitory concentrations of this compound required to inhibit the growth of the following bacteria are given below:

| Organisms | μg/ml (agar + 10% horse blood) |
|---|---|
| Citrobacter freundii C8 | 25 |
| Enterobacter cloacae N1 | 3.1 |
| Escherichia coli 0111 | 1.6 |
| Escherichia coli JT39 | 25 |
| Klebsiella aerogenes A | 1.6 |
| Proteus mirabilis C977 | 3.1 |
| Proteus rettgeri WM16 | 12.5 |
| Escherichia coli ESS | 0.4 |
| Salmonella typhimurium CT10 | 1.6 |
| Serratia marcescens US20 | 6.2 |
| Shigella sonnei MB 11967 | 1.6 |
| Bacillus subtilis A | 0.8 |
| Staphylococcus aureus Oxford | 3.1 |
| Staphylococcus aureus Russell | 6.2 |
| Streptococcus pyrogenes CN10 | 0.8 |
| Streptococcus pneumoniae CN33 | 0.1 |

EXAMPLE 13

5(R,S), 6(S,R)3-(4,6-Dimethyl-2-pyrimidylthio)-6-(1R-hydroxyethyl)-7-oxo-1-azabicyclo[3.2.0]hept-2-ene-2-carboxylate

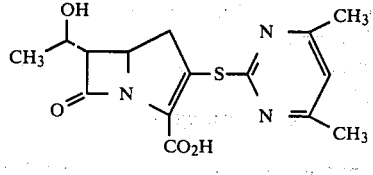

(i) Preparation of 3(R,S), 4(S,R) 4-(4,6-dimethyl-2-pyrimidylthiocarbonylmethyl)-3-(1R-p-nitrobenzyloxycarbonyloxyethyl)-1-(1-p-nitrobenzyloxycarbonyl-1-triphenylphosphoranylidenemethyl) azetidin-2-one

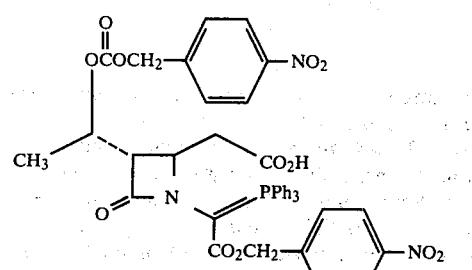

(4)

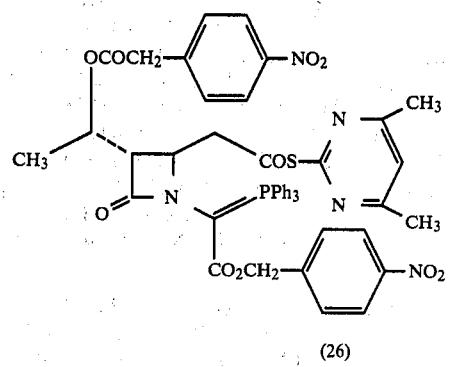

(26)

The phosphorane acid (4) (0.202 g) was dissolved in dry tetrahydrofuran (5 ml) and treated with triethylamine (0.026 g) followed by diethyl phosphorochloridate (0.048 g) in tetrahydrofuran (1 ml). The reaction was stirred at room temperature for two hours and treated with lithium 4,6 dimethyl-2-pyrimidylthiolate (0.038 g). The reaction was stirred at room temperature for one hour, the solution filtered and solvent evaporated. Chromatography of the residue on Merck Kieselgel 60 (>230 Mesh) using ethyl acetate as eluant gave the product (26) as a gum (0.175 g; 75%), $\nu_{max}$ (CHCl$_3$) 1750, 1720 (sh), 1625, 1610, 1590, 1525, 1440, 1350, cm$^{-1}$.

(ii) Preparation of 5(R,S),6(S,R) p-nitrobenzyl-3-(4,6-dimethyl-2-pyrimidylthio)-6-(1R-p-nitrobenzyloxycarbonyloxyethyl)-7-oxo-1-azabicyclo[3.2.0]hept-2-ene-2-carboxylate

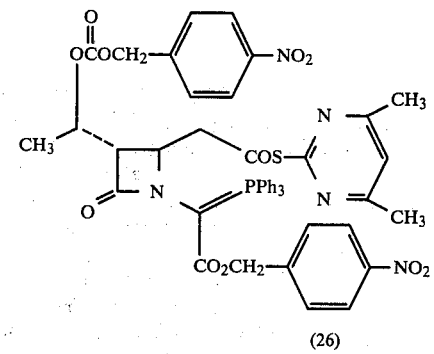

(26)

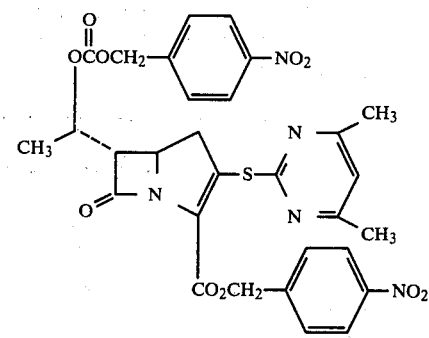

The thioester phosphorane (26) (0.13 g) was dissolved in dry toluene (140 ml) and refluxed vigorously under argon for 3½ hours. The solvent was evaporated and the residue chromatographed on Merck Kieselgel 60 (<230

Mesh) using petrol (60°-80°)/ethyl acetate as eluant to afford the product (27) as a white solid from ethyl acetate m.p. 165°-7° (0.5 g; 55%), $\lambda_{max}$ (EtOH) 264 nm ($\epsilon$14,800) 320 nm ($\epsilon$9100); $\nu_{max}$ (CHCl$_3$) 1785, 1735, 1605, 1585, 1525, 1345 cm$^{-1}$; $\delta$ppm (CDCl$_3$), 1.51 (3H, d, J 8 Hz, C$\underline{H}_3$-CH) 2.43 (6H, s, CH$_3$'s), 3.18 (1H, dd, J 9.5, 18 Hz, C4-H$_A$) 3.40 (1H, dd, J 2.5, 8 Hz, C6-H) 3.78 (1H, dd J 9.5, 18 Hz, C4-H$_B$) 4.25 (1H, m, C5-H) 4.95 to 5.60 (5H, m including s at 5.25, C$\underline{H}_2$ Ar, —OCO$_2$C$\underline{H}_2$ Ar and CH$_3$C$\underline{H}$) 6.79 (1H, s, pyrimidyl C4-H) 7.50 and 8.20 (4H, ABq, J 8.5 Hz, CH$_2$ Ar) 7.61 and 8.20 (4H, ABq, J 8.5 Hz, CH$_2$ Ar).

(iii) Preparation of 5(R,S), 6(S,R)-3-(4, 6 dimethyl-2-pyrimidythio)-6-(1R-hydroxyethyl)7-oxo-1-azabicyclo[3.2.0]hept-2 -ene-2-carboxylate

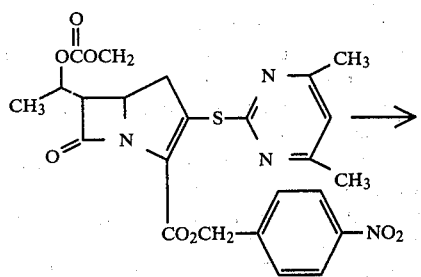

(27)

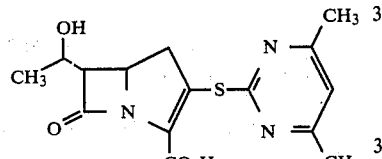

(28)

The p-nitrobenzyl ester (27) (0.036 g) was dissolved in dioxan (20 ml) containing ethanol (1 ml), deionised water (2.5 ml) and $^M$/20 phosphate buffer (3 ml). 10% Pd/C (0.06 g) was added to the solution and it was hydrogenated at ambient temperature and pressure for three hours. The solution was filtered through Kieselguhr and washed with water (5 ml). The filtrate was extracted with ether (3 = 15 ml). The aqueous phase was evaporated to provide the title product (28) as a white solid (0.015 g), $\lambda_{max}$ (H$_2$O) 301,246 nm; $\nu_{max}$ (KBr.) 1765, 1600, 1580, 1530, 1390, 1265 cm$^{-1}$.

The minimum inhibtory concentrations of this compound required to inhibit the growth of the following bacteria are given below:

| Organisms | μg/ml (D.S.T. Ager + Horse Blood) |
|---|---|
| *Citrobacter freundii* E8 | 25 |
| *Enterobacter cloacae* N1 | 12.5 |
| *Escherichia coli* 0111 | 12.5 |
| *Escherichia coli* JT89 | 5.0 |
| *Escherichia coli* ESS | 0.2 |
| *Klebsiella aerogenes* A | 2.5 |
| *Proteus mirabilis* C977 | 5.0 |
| *Proteus morganii* 1580 | 1.2 |
| *Salmonella typhimurium* CT10 | 5.0 |
| *Serratia marcescens* US20 | 12.5 |
| *Shigella Sonnei* MB 11967 | 5.0 |
| *Bacillus subtilis* A | 0.2 |
| *Staphylococcus aureus* Oxford | 0.5 |
| *Staphylococcus aureus* Russell | 0.5 |

-continued

| Organisms | μg/ml (D.S.T. Ager + Horse Blood) |
|---|---|
| *Staphylococcus aureus* 1517 | 5.0 |
| *Streptococcus faecalis* 1 | 5.0 |
| *Streptococcus pneumoniae* CN33 | 0.02 |
| *Streptococcus pyogenes* CN10 | 0.02 |

What we claim is:

1. A compound of the formula (II):

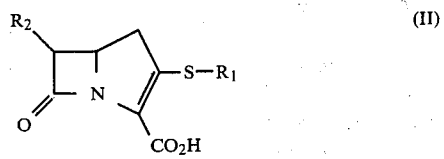

a salt thereof or an ester thereof which is convertible to a corresponding salt by chemical or biological means wherein R$_1$ is pyrimidyl unsubstituted or substituted by one or two lower alkyl groups, or by one lower alkoxy or lower alkanoyloxy group; and R$_2$ is hydrogen or a group CR$_3$R$_4$R$_5$ wherein R$_3$ is hydrogen or hydroxy; R$_4$ is hydrogen or lower alkyl, and R$_5$ is hydrogen, lower alkyl, benzyl or phenyl or is joined to R$_4$ to form part of a carbocyclic ring of 5 to 7 carbon atoms.

2. A compound according to claim 1 wherein R$_1$ is pyrimidyl unsubstituted or substituted by lower alkyl; and R$_2$ is hydrogen or CR$_3$R$_4$R$_5$ wherein R$_3$ is hydrogen or hydroxy; R$_4$ is hydrogen lower alkyl and R$_5$ is, benzyl, phenyl or is joined to R$_4$ to form part of a carbocyclic ring of 5 to 7 carbon atoms.

3. A compound according to claim 2 wherein R$_1$ is pyrimidyl, methylpyrimidyl, dimethylpyrimidyl, ethylpyrimidyl, diethylpyrimidyl or acetoxypyrimidyl.

4. A compound according to claim 3 wherein R$_1$ is 2-pyrimidyl, 4-pyrimidyl, 4-6-dimethyl-2-pyrimidyl or 4-methyl-2-pyrimidyl.

5. A compound according to claim 4 wherein R$_1$ is 2-pyrimidyl.

6. A compound according to claim 1 wherein R$_2$ is hydrogen.

7. A compound according to claim 1 wherein R$_2$ is CR$_3$R$_4$R$_5$ wherein R$_3$ is hydrogen or hydroxy, R$_4$ is hydrogen, methyl, ethyl or n-propyl and R$_5$ is hydrogen, methyl, ethyl, n-propyl or phenyl.

8. A compound of the formula (V):

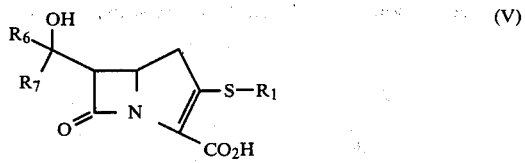

a salt thereof or an ester thereof which is convertible to a corresponding salt by chemical or biological means wherein R$_6$ is hydrogen or lower alkyl and R$_7$ is hydrogen or lower alkyl and R$_1$ is pyrimidyl unsubstituted or substituted by one or two lower alkyl groups or by a lower alkoxy or lower alkanoyloxy group.

9. A compound according to claim 8 wherein the C(OH)(R$_6$)R$_7$ moiety is a CH(CH$_3$)OH group.

10. A compound selected from the group consisting of: 5(R,S), 6(S,R)3-(4,6-Dimethyl-2-pyrimidylthio)-6-(1R-hydroxyethyl)-7-oxo-1-azabicyclo[3.2.0]hept- 2-ene-2-carboxylate, 5(R,S), 6(S,R) 3-(2-pyrimidylthio)-6-(1R-hydroxyethyl)-7-oxo-1-azabicyclo[3.2.0]hept-2-ene-2-carboxylate, benzyl 3-(2-pyrimidylthio)-7-oxo-1-azabicyclo[3.2.0]hept-2-ene-2-carboxylate,p-nitrobenzyl 3-(2-pyrimidylthio)-7-oxo-1-azabicyclo[3.2.0]hept-2-ene-2-carboxylate,phthalidyl 3-(4,6-dimethyl-2-pyrimidylthio)-7-oxo-1-azabicyclo[3.2.0]hept-2-ene-2-carboxylate, phthalidyl 3-(2-pyrimidylthio)-7-oxo-1-azabicyclo[3.2.0]hept-2-ene-2-carboxylate, benzyl 3-(4,6-dimethyl-2-pyrimidylthio)-7-oxo-1-azabicyclo[3.2.0]hept-2-ene-2-carboxylate, p-nitrobenzyl 3-(4,6-dimethyl-2-pyrimidylthio)-7-oxo-1-azabicyclo[3.2.0]hept-2-ene-2-carboxylate, benzyl 3-(4-pyrimidylthio)-7-oxo-1-azabicyclo[3.2.0]hept-2-ene-2-carboxylate, p-nitrobenzyl 3-(4-pyrimidylthio)-7-oxo-1-azabicyclo[3.2.0]hept-2-ene-2-carboxylate, 3-(2-pyrimidylthio)-7-oxo-1-azabicyclo[3.2.0]hept-2-ene-2-carboxylate, 3-(4,6-dimethyl-2-pyrimidylthio)-7-oxo-1-azabicyclo[3.2.0]hept-2-ene-2-carboxylate, p-nitrobenzyl 3-(4-methyl-2-pyrimidylthio)-7-oxo-1-azabicyclo[3.2.0]-hept-2-ene-2-carboxylate, 3-(4-methyl-2-pyrimidylthio)-7-oxo-1-azabicyclo[3.2.0]hept-2-ene-2-carboxylate, 5(R,S), 6(S,R)3-(4-pyrimidylthio)-6-(1R-hydroxyethyl)-7-oxo-1-azabicyclo[3.2.0]hept-2-ene-2-carboxylate, and 5(R,S), 6(S,R) 3-(4-methyl-2-pyrimidylthio)-(1R-hydroxyethyl)-7-oxo-1-azabicyclo[3.2.0]hept-2-ene-2-carboxylate.

11. A compound according to claim 1 wherein the ester group is of the sub-formulae (a), (b), (c) or (d):

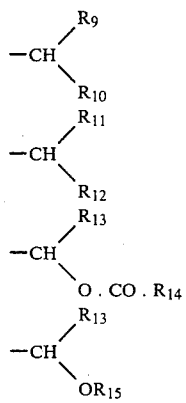

wherein $R_9$ is hydrogen, or alkyl, alkenyl or alkynyl of up to 3 carbon atoms; $R_{10}$ is hydrogen or methyl; $R_{11}$ is phenyl unsubstituted or substituted by fluorine, chlorine, bromine, nitro, methyl or methoxy; $R_{12}$ is hydrogen or phenyl unsubstituted or substituted by fluorine, chlorine, bromine nitro, methyl or methoxy; $R_{13}$ is hydrogen or methyl and $R_{14}$ is lower alkyl, phenyl or lower alkoxy or $R_{13}$ is joined to $R_{14}$ to form a phthalidyl group, and $R_{15}$ is lower alkyl, phenyl, chlorophenyl or nitrophenyl.

12. A compound according to claim 1 when in zwitterionic form.

13. A compound according to claim 1 wherein there is cis-configuration about the β-lactam ring.

14. A compound according to claim 1 wherein there is trans-configuration about the β-lactam ring.

15. A compound according to claim 1 wherein $R_1$ is 2-pyrimidyl, dimethyl-4-pyrimidyl or methyl-2-pyrimidyl.

16. A compound according to claim 7 wherein $R_3$ is hydroxyl.

17. A compound according to claim 7 wherein $R_4$ is hydrogen or methyl.

18. A compound according to claim 7 wherein $R_5$ is hydrogen or methyl.

19. A compound according to claim 7 wherein $R_3$ is hydroxyl, $R_4$ is hydrogen or methyl and $R_5$ is hydrogen or methyl.

20. A compound according to claim 8 wherein $R_6$ is hydrogen, methyl or ethyl and $R_7$ is hydrogen, methyl or ethyl.

21. A compound according to claim 8 wherein the $C(OH)(R_6)R_7$ moiety is $C(CH_3)_2OH$, $CH(CH_3)OH$ or $CH(C_2H_5)OH$.

22. A compound according to claim 8 wherein the $C(OH)(R_6)R_7$ moiety is $CH(CH_3)OH$ and $R_1$ is 2-pyrimidyl, dimethyl-4-pyrimidyl or methyl-2-pyrimidyl.

23. A compound according to claim 1 wherein the compound is of the formula (VI):

$$R_8-H_2C \quad \underset{O}{\overset{}{\bigsqcup}} \quad \overset{S-R_1}{\underset{CO_2H}{\bigvee}} \qquad (VI)$$

a salt thereof or an ester thereof which is convertible to a corresponding salt by chemical or biological means wherein $R_1$ is pyrimidyl unsubstituted or substituted by one or two lower alkyl groups or by one lower alkoxy or by lower alkanoyloxy group and $R_8$ is hydrogen, methyl or ethyl.

24. A compound according to claim 1 in the form of a sodium salt.

25. A compound according to claim 1 wherein $R_1$ is dimethylpyrmidyl.

26. A compound according to claim 1 in the form of a salt wherein salt is the sodium, potassium calcium, magnesium, lithium, ammonium or barium salt.

27. A pharmaceutical composition useful for treating bacterial infections in humans and animals which comprises an antibacterially effective amount of a compound of the formula (II):

$$R_2 \quad \underset{O}{\overset{}{\bigsqcup}} \quad \overset{S-R_1}{\underset{CO_2H}{\bigvee}} \qquad (II)$$

a pharmaceutically acceptable salt thereof or a pharmaceutically acceptable ester thereof wherein $R_1$ is pyrimidyl unsubstituted or substituted by one or two lower alkyl groups, or by a lower alkoxy or lower alkanoyloxy group; and $R_2$ is hydrogen or a group $CR_3R_4R_5$ wherein $R_3$ is hydrogen or hydroxy; $R_4$ is hydrogen or lower alkyl, and $R_5$ is hydrogen, lower alkyl, benzyl or phenyl or is joined to $R_4$ to form part of a carbocyclic ring of 5 to 7 carbon atoms, in combination with a pharmaceutically acceptable carrier.

28. A composition according to claim 27 wherein $R_1$ is pyrimidyl unsubstituted or substituted by lower alkyl and $R_2$ is hydrogen or $CR_3R_4R_5$ wherein $R_3$ is hydrogen or hydroxy, $R_4$ is hydrogen, lower alkyl, benzyl, phenyl or is joined to $R_4$ to form part of a carbocyclic ring of 5 to 7 carbon atoms.

29. A composition according to claim 27 wherein $R_1$ is pyrimidyl, methylpyrimidyl, dimethylpyrimidyl, ethylpyrimidyl, diethylpyrimidyl or acetoxypyrimidyl.

30. A composition according to claim 27 wherein $R_1$ is 2-pyrimidyl, 4-pyrimidyl, 4,6-dimethyl-2-pyrimidyl or 4-methyl-2-pyrimidyl.

31. A composition according to claim 27 wherein $R_1$ is 2-pyrimidyl.

32. A composition according to claim 27 wherein $R_2$ is hydrogen.

33. A composition according to claim 27 wherein $R_2$ is $CR_3R_4R_5$ wherein $R_3$ is hydrogen or hydroxy, $R_4$ is hydrogen, methyl, ethyl or n-propyl and $R_5$ is hydrogen, methyl, ethyl, n-propyl or phenyl.

34. A composition according to claim 33 wherein the compound is of formula (V):

a pharmaceutically acceptable salt thereof or a pharmaceutically acceptable ester thereof wherein $R_6$ is hydrogen or lower alkyl and $R_7$ is hydrogen or lower alkyl and $R_1$ is pyrmidyl unsubstituted or substituted by one or two lower alkyl groups or by a lower alkoxy or lower alkanoyloxy.

35. A composition according to claim 27 wherein the $C(OH)(R_6)R_7$ moiety is a $CH(CH_3)OH$ group.

36. A composition according to claim 27 wherein the compound is selected from the group consisting of: 5(R,S), 6(S,R)3-(4,6-Dimethyl-2-pyrimidylthio)-6-(1R-hydroxyethyl)-7-oxo-1-azabicyclo[3.2.0]hept-2-ene-2-carboxylate. 5(R,S), 6(S,R) 3-(2-pyrimidylthio)-6-(R-hydroxyethyl)-7-oxo-1-azabicyclo[3.2.0]hept-2-ene-2-carboxylate, benzyl 3-(2-pyrimidylthio)-7-oxo-1-azabicyclo[3.2.0]hept-2-ene-2-carboxylate, p-nitrobenzyl 3-(2-pyrimidylthio)-7-oxo-1-azabicyclo[3.2.0]hept-2-ene-2-carboxylate, phthalidyl 3-(4,6-dimethyl-2-pyrimidylthio)-7-oxo-1-azabicyclo[3.2.0]hept-2-ene-2-carboxylate, phthalidyl 3-(2-pyrimidylthio)-7-oxo-1-azabicyclo[3.2.0]hept-2-ene-2-carboxylate, benzyl 3-(4,6-dimethyl-2-pyrimidylthio)-7-oxo-1-azabicyclo[3.2.0]hept-2-ene-2-carboxylate, p-nitrobenzyl 3-(4,6-dimethyl-2-pyrimidylthio)-7-oxo-1-azabicyclo[3.2.0]hept-2-ene-2-carboxylate, benzyl 3-(4-pyrimidylthio)-7-oxo-1-aza-bicyclo[3.2.0]hept-2-ene-2-carboxylate, p-nitrobenzyl 3-(4-pyrimidylthio)-7-oxo-1-azabicyclo[3.2.0]hept-2-ene-2-carboxylate, 3-(2-pyrimidylthio)-7-oxo-1-azabicyclo [3.2.0]hept-2-ene-2-carboxylate, 3-(4,6-dimethyl-2-pyrimidylthio)-7-oxo-1-azabicyclo[3.2.0]hept-2-ene-2-carboxylate, p-nitrobenzyl 3-(4-methyl-2-pyrimidylthio)-7-oxo-1-azabicyclo [3.2.0]-hept-2-ene-2-carboxylate, 3-(4-methyl-2-pyrimidylthio)-7-oxo-1-azabicyclo[3.2.0]hept-2-ene-2-carboxylate, 5(R,S), 6(S,R)-3-(4-pyrimidylthio)-6-(1R-hydroxyethyl)-7-oxo-1-azabicyclo[3.2.0]hept-2-ene-2-carboxylate, and 5(R,S), 6(S,R) 3-(4-methyl-2-pyrimidylthio)-(1R-hydroxyethyl)-7-oxo-1-azabicyclo[3.2.0]hept-2-ene-2-carboxylate.

37. A composition according to claim 27 wherein the ester group is of the sub-formulae (a), (b), (c) or (d):

wherein $R_9$ is hydrogen or alkyl, alkenyl or alkynyl of up to 3 carbon atoms; $R_{10}$ is hydrogen or methyl; $R_{11}$ is phenyl unsubstituted of substituted by fluorine, chlorine, bromine, nitro, methyl or methoxy; $R_{12}$ is hydrogen or phenyl unsubstituted or substituted by fluorine, chlorine, bromine, nitro, methyl or methoxy; $R_{13}$ is hydrogen or methyl and $R_{14}$ is lower alkyl, phenyl or lower alkoxy or $R_{13}$ is joined to $R_{14}$ to form a phthalidyl group; and $R_{15}$ is lower alkyl, phenyl, chlorophenyl or nitrophenyl.

38. A composition according to claim 27 wherein the compound is in zwitterionic form.

39. A composition according to claim 27 wherein the compound has a cis-configuration about the β-lactam ring.

40. A composition according to claim 27 wherein the compound has a trans-configuration about the β-lactam ring.

41. A composition according to claim 33 wherein $R_1$ is 2-pyrimidyl, -dimethyl-4-pyrimidyl or methyl-2-pyrimidyl.

42. A composition according to claim 33 wherein $R_3$ is hydroxyl.

43. A composition according to claim 33 wherein $R_4$ is hydrogen or methyl.

44. A composition according to claim 33 wherein $R_5$ is hydrogen or methyl.

45. A composition according to claim 34 wherein $R_3$ is hydroxyl, $R_4$ is hydrogen or methyl and $R_5$ is hydrogen or methyl.

46. A composition according to claim 34 wherein $R_6$ is hydrogen, methyl or ethyl and $R_7$ is hydrogen, methyl or ethyl.

47. A composition according to claim 34 wherein the $C(OH)(R_6)R_7$ moiety is $C(CH_3)_2OH$, $CH(CH_3)OH$ or $CH(C_2H_5)OH$.

48. A composition according to claim 27 wherein the $C(OH)(R_6)R_7$ moiety is $CH(CH_3)OH$ and $R_1$ is 2-pyrimidyl, dimethyl-4-pyrimidyl or methyl-2-pyrimidyl.

49. A composition according to claim 27 wherein the compound is of the formula (VI):

or a pharmaceutically acceptable salt or pharmaceutically acceptable ester thereof wherein $R_1$ is pyrimidyl unsubstituted or substituted by one or two lower alkyl groups or by a lower alkoxy or lower alkanoyloxy and $R_8$ is hydrogen, methyl or ethyl.

50. A composition according to claim 27 in oral administration form.

51. A composition according to claim 27 in parenteral administration form.

52. A composition according to claim 27 suitable for administration to cattle in intramammary injection form.

53. A composition according to claim 27 wherein $R_1$ is pyrimidyl substituted by 2 lower alkyl groups.

54. A composition according to claim 27 wherein $R_1$ is dimethylpyrimidyl.

55. A composition according to claim 27 wherein the compound is in the form of the sodium, potassium, calcium, magnesium or ammonium salt.

56. A method of treating bacterial infections in humans and animals which comprises administering to a human or animal in need thereof an antibacterially effective amount of a compound of the formula (II):

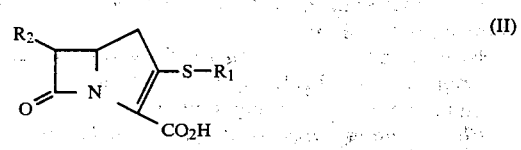

a pharmaceutically acceptable salt thereof or a pharmaceutically acceptable ester thereof wherein $R_1$ is pyrimidyl unsubstituted or substituted by one or two lower alkyl groups, or by a lower alkoxy or lower alkanoyloxy; and $R_2$ is hydrogen or a group $CR_3R_4R_5$ wherein $R_3$ is hydrogen or hydroxy; $R_4$ is hydrogen or lower alkyl, and $R_5$ is hydrogen, lower alkyl, benzyl or phenyl or is joined to $R_4$ to form part of a carbocyclic ring of 5 to 7 carbon atoms.

57. A method according to claim 56 wherein $R_1$ is pyrimidyl unsubstituted or substituted by lower alkyl and $R_2$ is hydrogen or $CR_3R_4R_5$ wherein $R_3$ is hydrogen or hydroxy, $R_4$ is hydrogen, lower alkyl, benzyl, phenyl or is joined to $R_4$ to form part of a carbocyclic ring of 5 to 7 carbon atoms.

58. A method according to claim 56 wherein $R_1$ is pyrimidyl, methylpyrimidyl, dimethylpyrimidyl, ethylpyrimidyl, diethylpyrimidyl or acetoxypyrimidyl.

59. A method according to claim 56 wherein $R_1$ is 2-pyrimidyl, 4-pyrimidyl, 4,6-dimethyl-2-pyrimidyl or 4-methyl-2-pyrimidyl.

60. A method according to claim 56 wherein $R_1$ is 2-pyrimidyl.

61. A method according to claim 56 wherein $R_2$ is hydrogen.

62. A method according to claim 56 wherein $R_2$ is $CR_3R_4R_5$ wherein $R_3$ is hydrogen or hydroxy, $R_4$ is hydrogen, methyl, ethyl of n-propyl and $R_5$ is hydrogen, methyl, ethyl, n-propyl of phenyl.

63. A method according to claim 56 wherein the compound is of the formula (V):

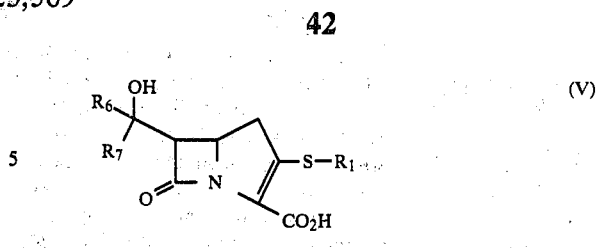

a pharmaceutically acceptable salt thereof or a pharmaceutically acceptable ester thereof wherein $R_6$ is hydrogen or lower alkyl and $R_7$ is hydrogen or lower alkyl and $R_1$ is pyrimidyl unsubstituted or substituted by one or two lower alkyl groups or by a lower alkoxy or lower alkanoyloxy.

64. A method according to claim 56 wherein the $C(OH)(R_6)R_7$ moiety is a $CH(CH_3)OH$ group.

65. A method according to claim 56 wherein the compound is selected from the group consisting of: 5(R,S), 6(S,R)3-(4,6-Dimethyl-2-pyrimidylthio)-6-(1R-hydroxyethyl)-7-oxo-1-azabicyclo[3.2.0]hept-2-ene-2-carboxylate, 5(R,S), 6(S,R) 3-(2-pyrimidylthio)-6-(1R-hydroxyethyl)-7-oxo-1-azabicyclo[3.2.0]hept-2-ene-2-carboxylate, benzyl 3-(2-pyrimidylthio)-7-oxo-1-azabicycl[3.2.0]hept-2-ene-2-carboxylate, p-nitrobenzyl 3-(2-pyrimidylthio)-7-oxo-1-azabicyclo[3.2.0]hept-2-ene-2-carboxylate, phthalidyl 3-(4,6-dimethyl-2-pyrimidylthio)-7-oxo-1-azabicyclo[3.2.0]hept-2-ene-2-carboxylate, phthalidyl 3-(2-pyrimidylthio)-7-oxo-1-azabicyclo[3.2.0]hept-2-ene-2-carboxylate, benzyl 3-(4,6-dimethyl-2-pyrimidylthio)-7-oxo-1-azabicyclo[3.2.0]hept-2-ene-2-carboxylate, p-nitrobenzyl 3-(4,6-dimethyl-2-pyrimidylthio)-7-oxo-1-azabicyclo [3.2.0]hept-2-ene-2-carboxylate, benzyl 3-(4-pyrimidylthio)-7-oxo-1-azabicyclo[3.2.0]hept-2-ene-2-carboxylate, p-nitrobenzyl 3-(4-pyrimidylthio)-7-oxo-1-azabicyclo[3.2.0]hept-2-ene-2-carboxylate, 3-(2-pyrimidylthio)-7-oxo-1-azabicyclo [3.2.0]hept-2-ene-2-carboxylate, 3-(4,6-dimethyl-2-pyrimidylthio)-7-oxo-1-azabicyclo[3.2.0]hept-2-ene-2-carboxylate, p-nitrobenzyl 3-(4-methyl-2-pyrimidylthio)-7-oxo-1-azabicyclo [3.2.0]-hept-2-ene-2-carboxylate, 3-(4-methyl-2-pyrimidylthio)-7-oxo-1-azabicyclo[3.2.0]hept-2-ene-2-carboxylate, 5(R,S), 6(S,R)3-(4-pyrimidylthio)-6-(1R-hydroxyethyl)-7-oxo-1-azabicyclo[3.2.0]hept-2-ene-2-carboxylate, and 5(R,S), 6(S,R) 3-(4-methyl-2-pyrimidylthio)-1R-hydroxyethyl)-7-oxo-1-azabicyclo[3.2.0]hept-2-ene-2-carboxylate.

66. A method according to claim 63 wherein the ester group is of the sub-formulae (a), (b), (c) or (d):

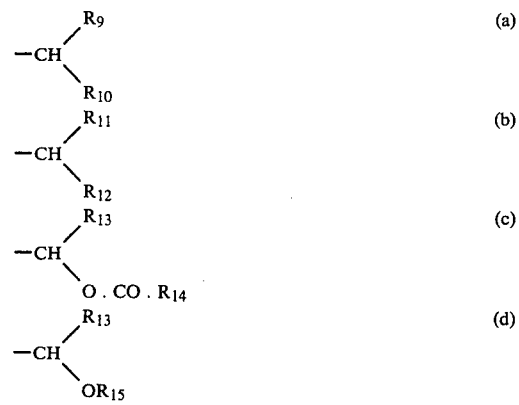

wherein R_9 is hydrogen or alkyl, alkenyl or alkynyl of up to 3 carbon atoms; R_{10} is hydrogen or methyl; R_{11} is phenyl unsubstituted of substituted by fluorine, chlorine, bromine, nitro, methyl or methoxy; R_{12} is hydrogen or phenyl unsubstituted or substituted by fluorine, chlorine, bromine, nitro, methyl or methoxy; R_{13} is hydrogen or methyl and R_{14} is lower alkyl, phenyl or lower alkoxy or R_{13} is joined to R_{14} to form a phthalidyl group; and R_{15} is lower alkyl, phenyl, chlorophenyl or nitrophenyl.

67. A method according to claim 56 wherein the compound is in zwitterionic form.

68. A method according to claim 56 wherein the compound has a cis-configuration about the β-lactam ring.

69. A method according to claim 56 wherein the compound has a trans-configuration about the β-lactam ring.

70. A method according to claim 56 wherein R_1 is 2-pyrimidyl, dimethyl-4-pyrimidyl or -methyl-2-pyrimidyl.

71. A method according to claim 56 wherein R_3 is hydroxyl.

72. A method according to claim 56 wherein R_4 is hydrogen or methyl.

73. A method according to claim 62 wherein R_5 is hydrogen or methyl.

74. A method according to claim 62 wherein R_3 is hydroxyl, R_4 is hydrogen or methyl and R_5 is hydrogen or methyl.

75. A method according to claim 62 wherein R_6 is hydrogen, methyl or ethyl and R_7 is hydrogen, methyl or ethyl.

76. A method according to claim 62 wherein the C(OH)(R_6)R_7 moiety is C(CH_3)_2OH, CH(CH_3)OH or CH(C_2H_5)OH.

77. A method according to claim 63 wherein the C(OH)(R_6)R_7 moiety is CH(CH_3)OH and R_1 is 2-pyrimidyl, dimethyl-4-pyrimidyl or methyl-2-pyrimidyl.

78. A method according to claim 56 wherein the compound is of the formula (VI):

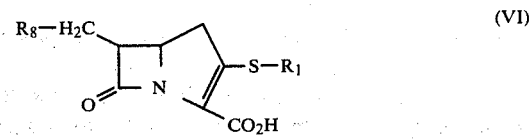

or a pharmaceutically acceptable salt or pharmaceutically acceptable ester thereof wherein R_1 is pyrimidyl unsubstituted or substituted by one or two lower alkyl groups or by a lower alkoxy or lower alkanoyloxy and R_8 is hydrogen, methyl or ethyl.

79. A method according to claim 63 wherein the administration is oral.

80. A method according to claim 56 wherein the administration is parentral.

81. A method according to claim 56 wherein the administration is to cattle by intra-mammary injection.

82. A method according to claim 56 wherein R_1 is pyrimidyl substituted by 2 lower alkyl groups.

83. A method according to claim 56 wherein R_1 is dimethylpyrimidyl.

84. A method according to claim 56 wherein the compound is in the form of the sodium, potassium, calcium, magnesium or ammonium salt.

85. A composition according to claim 21 wherein the compound is in the form of a sodium salt.

86. A method according to claim 56 wherein the compound is in the form of a sodium salt.

* * * * *